United States Patent

Yamatsu et al.

[11] Patent Number: 4,639,450
[45] Date of Patent: Jan. 27, 1987

[54] POLYPRENYLCARBOXYLIC ACID MORPHOLIDES AND PHARMACEUTICAL COMPOSITIONS

[75] Inventors: Isao Yamatsu, Kawaguchi; Yuichi Inai; Shinya Abe, both of Tokyo; Hideaki Watanabe, Aichi; Toshiji Igarashi, Tokorozawa; Hiroyuki Shiojiri, Sayama; Yoshio Tanabe, Saitama; Kumiko Hara, Tokyo, all of Japan

[73] Assignee: Eisai Co., Ltd., Tokyo, Japan

[21] Appl. No.: 677,893

[22] Filed: Dec. 4, 1984

Related U.S. Application Data

[60] Continuation of Ser. No. 503,205, Jun. 10, 1983, abandoned, which is a division of Ser. No. 175,213, Aug. 4, 1980, Pat. No. 4,456,603.

[30] Foreign Application Priority Data

Aug. 14, 1979 [JP] Japan .................. 54-102747
Aug. 28, 1979 [JP] Japan .................. 54-108668

[51] Int. Cl.$^4$ .................. A61K 31/535; C07D 295/18
[52] U.S. Cl. .................. 514/238; 544/176
[58] Field of Search .................. 544/176; 514/238

[56] References Cited

U.S. PATENT DOCUMENTS

| | | | |
|---|---|---|---|
| 3,147,261 | 9/1964 | Mod et al. | 544/176 |
| 3,270,033 | 8/1966 | Skau et al. | 260/326.5 E |
| 3,294,794 | 12/1966 | Holmes et al. | 544/176 |
| 3,404,145 | 10/1968 | Skau et al. | 260/326.5 E |
| 3,621,043 | 11/1971 | Seki et al. | 544/176 |
| 3,649,590 | 3/1972 | Siddall | 260/326.5 E |
| 3,773,805 | 11/1973 | Siddall | 260/326.5 E |

*Primary Examiner*—Robert W. Ramsuer
*Attorney, Agent, or Firm*—Flynn, Thiel, Boutell & Tanis

[57] ABSTRACT

This invention relates to polyprenylcarboxylic acid amides represented by the following general formula (I):

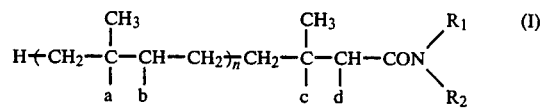

wherein n is an integer of from 1 to 4, a and b stand for hydrogen atoms or a direct valence bond between the carbon atoms to which a and b are attached, c and d stand for hydrogen atoms or a direct valence bond between the carbon atoms to which c and d are attached, and $R_1$ and $R_2$ stand for a hydrogen atom, a lower alkyl group, a phenyl group which may be substituted or an aralkyl group which may be substituted, or $R_1$ and $R_2$ form, together with the adjacent nitrogen atom, a 5- or 6-membered heterocyclic ring which may contain other hetero atoms or may be substituted, and also to a process for the preparation of said polyprenylcarboxylic acid amide and to a pharmaceutical composition for treating liver dysfunction comprising said polyprenylcarboxylic acid amide.

4 Claims, No Drawings

POLYPRENYLCARBOXYLIC ACID MORPHOLIDES AND PHARMACEUTICAL COMPOSITIONS

This application is a continuation of U.S. Ser. No. 503,205, filed June 10, 1983, now abandoned which is a division of U.S. Ser. No. 175,213, filed Aug. 4, 1980 now U.S. Pat. No. 4,456,603.

The present invention relates to polyprenylcarboxylic acid amides represented by the following general formula (I):

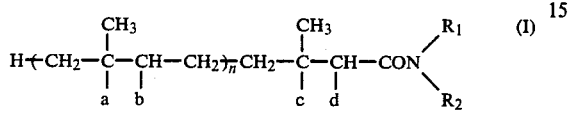

wherein n is an integer of from 1 to 4, a and b stand for hydrogen atoms or a direct valence bond between the carbon atoms to which a and b are attached, c and d stand for hydrogen atoms or a direct valence bond between the carbon atoms to which c and d are attached, and $R_1$ and $R_2$ stand for a hydrogen atom, a lower alkyl group, a phenyl group which may be substituted or an aralkyl group which may be substituted, or $R_1$ and $R_2$ form, together with the adjacent nitrogen atom, a 5- or 6-membered heterocyclic ring which may contain other hetero atoms or may be substituted, and also to a process for the preparation of said polyprenylcarboxylic acid amide and to a pharmaceutical composition for treating liver dysfunction comprising said polyprenylcarboxylic acid amide.

In the above-mentioned general formula (I), $R_1$ and $R_2$ stand for a hydrogen atom, a lower alkyl group such as a methyl group, an ethyl group, an iso-propyl group, an n-propyl group, a t-butyl group or an n-butyl group, a phenyl group, or an aralkyl group such as a benzyl group or a phenylethyl group. These phenyl and aralkyl groups can be ring substituted with a lower alkyl group, a hydroxyl group, an alkoxy group, a methylene-dioxy group or a halogen atom. Furthermore,

can form a 5- or 6-membered heterocyclic ring.

As such heterocyclic ring, there can be mentioned a morpholino group, a 1-pyrrolidinyl group, a piperidino group and a 1-piperazinyl group. These heterocyclic rings can be ring substituted with a lower alkyl group, an alkoxy group, a hydroxy-lower-alkyl group, a phenyl group, an alkoxyphenyl group, a hydroxyl group, a formyl group or a halogen atom.

The compounds of the present invention can be prepared according to the following processes.

PROCESS A

A compound represented by the following general formula (I-1):

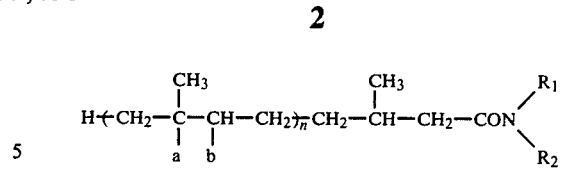

wherein n, a, b, $R_1$ and $R_2$ are as defined above, is prepared according to a process comprising (a) reacting a compound represented by the following general formula (V):

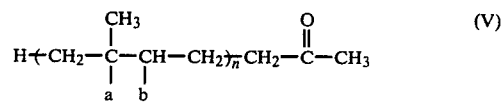

wherein n, a and b are as defined above, with a lower alkyl ester of cyanoacetic acid, in the presence of a base, to form a compound represented by the following general formula (VI):

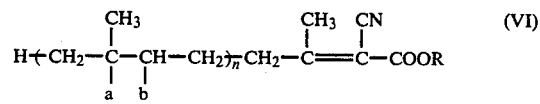

wherein n, a and b are as defined above, and R stands for a lower alkyl group, (b) reducing the compound represented by the general formula (VI) to obtain a compound represented by the following general formula (VII):

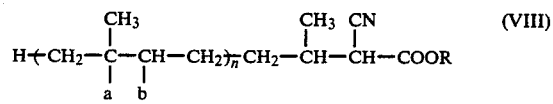

wherein n, a and b are as defined above, (c) decarboxylating the compound represented by the general formula (VII), in the presence of a base, such as potassium hydroxide, sodium hydroxide or pyridine-copper, and hydrolyzing the decarboxylated compound to form a compound represented by the following general formula (II):

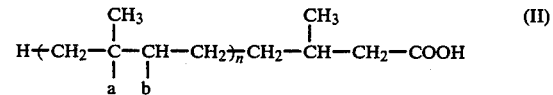

wherein n, a and b are as defined above, and (d) reacting the compound represented by the general formula (II), or a reactive derivative thereof, with a compound represented by the following general formula (III):

wherein $R_1$ and $R_2$ are as defined above.

The amide synthesis reaction of the step (d) can be performed according to a conventional method. When the carboxylic acid of the general formula (II) is used, it is preferred that the reaction be carried out in the presence of a dehydrating condensating agent such as N,N'-dicyclocarbodiimide, N,N'-diethylcarbodiimide, a trialkyl ester of phosphorous acid, an ethyl ester of polyphosphoric acid, phosphorus oxychloride, oxazolyl chloride or tosyl chloride. When a reactive derivative of the compound of the general formula (II) is used, as the reaction derivatives in which the carboxyl group is modified there are used, for example, acid halides such as acid chloride and acid bromide, corresponding acid anhydrides, mixed acid anhydrides with such carboxylic acids as chlorocarbonic acid ester, trimethylacetic acid, thioacetic acid and diphenylacetic acid, active esters with 2-mercaptopyridine, cyanomethanol, p-nitrophenol, 2,4-dinitrophenol and pentachlorophenol, active acid amides with N-acylsaccharin and N-acylsulfonamide, and acid azides. This amide synthesis reaction can be carried out in a solvent, for example, an ether, such as diethyl ether, tetrahydrofuran or dioxane, a halogenated hydrocarbon, such as dichloromethane or chloroform, or an aromatic hydrocarbon, such as benzene or toluene, in the presence of or in the absence of a basic reagent, such as triethylamine or pyridine.

In the step (d), if the compound of the general formula (III) contains another functional group capable of reacting with the compound of the general formula (II), the intended compound can be obtained by reacting such a compound of formula (III) in which said another group is protected with a protecting group, with the compound of the general formula (II) and then isolating the protecting group from the resulting compound. For example, in case of piperazine, N-formylpiperazine is reacted to effect amidation and then, deformylation is carried out.

PROCESS B

A compound of the present invention, which is represented by the following general formula (I-2):

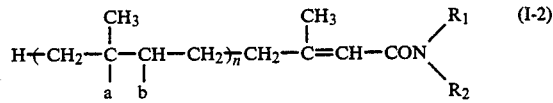

wherein a, b, R₁ and R₂ are as defined above, can be obtained by reacting a compound represented by the following general formula (V):

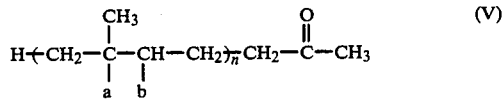

wherein n, a and b are as defined above, with a Wittig reagent derived from a compound represented by the following general formula (VIII):

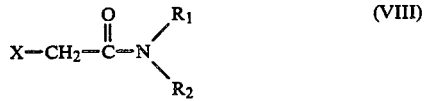

wherein X stands for a halogen atom, and R₁ and R₂ are as defined above.

As the Wittig reagent derived from a compound of the general formula (VIII), there can be mentioned compounds represented by the following general formulae (IX), (X) and (XI), which are obtained by reacting the compound of the general formula (VIII) with a trialkyl phosphite, a phenyldialkoxyphosphine and a triphenylphosphine, respectively:

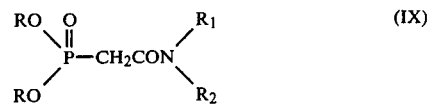

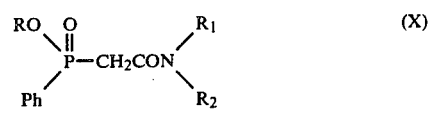

and

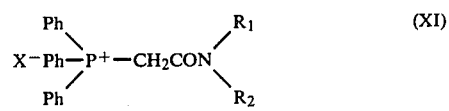

wherein R stands for an alkyl group, Ph stands for phenyl group, and R₁, R₂ and X are as defined above.

These Wittig reagents can be prepared according to conventional methods, for example, the method of Wadworth et al. [see J. Am. Chem. Soc., 83, page 1733 (1961)], the method of Greenwald et al. [see J. Org. Chem., 28, page 1128 (1963)], and the method of Horner et al. [see Ber., 95, page 581 (1962)].

The reaction of the Wittig reagent with the compound of the general formula (V) can be carried out according to a conventional Wittig reaction method, for example, the methods disclosed in the above literature references.

The reaction is ordinarily carried out in the presence of a basic reagent such as butyl lithium, sodium amide, sodium hydride, sodium methylate, potassium t-butoxide, potassium hydroxide, sodium carbonate or triethylamine. Benzene, xylene, n-hexane, petroleum ether, isopropyl ether, dioxane, tetrahydrofuran, ethyl acetate, dimethylformamide or the like is used as the solvent.

The compound of the general formula (VIII) can be obtained by reacting a compound represented by the following general formula (III):

wherein R₁ and R₂ are as defined above, with a haloacetyl halide in a solvent, such as pyridine or triethylamine.

If the compound of the general formula (III) contains another functional group capable of reacting with the haloacetyl halide, such a compound of formula (III) in which said another functional group is protected with a protecting group is reacted with the haloacetyl halide to form a Wittig reagent, and after the Wittig reaction, the protecting group is isolated whereby the intended compound can be obtained. For example, in the case where the compound of the general formula (XII) is piperazine, 1-formylpiperazine is used and the formyl group is finally isolated.

PROCESS C

The compound of the general formula (I-2), prepared according to the above-mentioned process B, is reduced whereby a compound of the general formula (I-1) can be obtained.

If this reducing reaction is catalytically carried out, all the double bonds in the isoprene chain of the compound of the general formula (I-2) are reduced. When the reducing reaction is carried out by using sodium borohydride and a metal halide, only the double bond adjacent to the carbonyl group of the compound of the general formula (I-2) is reduced. These methods are appropriately chosen according to the compound intended to be obtained.

The catalytic reduction is accomplished in an inert solvent, such as tetrahydrofuran, benzene, toluene, dichloromethane, ethanol or dioxane, in the presence of a catalyst such as palladium-carbon or Raney nickel, while introducing hydrogen gas. The reduction with sodium borohydride and a metal halide is carried out in an alcoholic solvent, such as methanol or ethanol, in the presence of sodium borohydride and a metal halide, such as nickel chloride, cobalt chloride or copper chloride.

The compound of the present invention is valuable as an agent for treatment of liver dysfunction. The liver undergoes dysfunctions such as inflammation, degeneration, devastation, anacholia and abnormal saccharometabolism, which are caused by various factors such as alcohol, lack of nourishment, virus, chemical substances and toxins. The compound of the present exerts an effect of moderating or preventing these dysfunctions.

Results of the pharmacological tests made on various compounds included in the scope of the present invention will now be described.

TEST COMPOUNDS 4-(3,7,11-trimethyldodecanoyl)morpholine (compound A)

4-[(E)-3,7,11-trimethyl-6,10-dodecadienoyl]morpholine (compound B)

4-(3,7,11,15-tetramethylhexadecanoyl)morpholine (compound C)

4-[(E,E)-3,7,11,15-tetramethyl-6,10,14-hexadecatrienoyl]morpholine (compound D)

(E,E)-3,7,11,15-tetramethyl-6,10,14-hexadecatrienamide (compound E)

(E,E)-N,N-diemthyl-3,7,11,15-tetramethyl-6,10,14-hexadecatrienamide (compound F)

1-[(E,E)-3,7,11,15-tetramethyl-6,10,14-hexadecatrienoyl]-4-(2-hydroxyethyl)piperazine (compound G)

4-(3,7,11-trimethyl-2-dodecaenoyl)morpholine (compound H)

4-(3,7,11,15-tetramethyl-2-hexadecaenoyl)morpholine (compound I)

3,7,11,15-tetramethyl-2,6,10,14-hexadecatetraenamide (compound J)

N,N-dimethyl-3,7,11,15-tetramethyl-2,6,10,14-hexadecatetraenamide (compound K)

1-(3,7,11,15-tetramethyl-2,6,10,14-hexadecatetraenoyl)-4-(2-hydroxyethyl)piperazine (compound L)

4-(3,7,11,15-tetramethyl-2,6,10,14-hexadecatetraenoyl)morpholine (compound M)

EXPERIMENT I

The effect on the liver dysfunction (hepatitis) induced by D-galactosamine by administration into the abdominal cavity was examined.

Rats of the SD series having a body weight of about 250 g were used as test animals. D-Galactosamine hydrochloride (250 mg/Kg each time) and the test compound (50 mg/Kg each time) were administered into the abdominal cavity according to the schedule described below. After termination of the experiment, blood was collected from the test animals, and the GOT value, GPT value and alkali phosphatase value, which are indicators of the degree of the liver dysfunction, were measured.

The test compound was suspended in a 5% aqueous solution of gum arabic and was administered in the form of the suspension. D-Galactosamine hydrochloride was dissolved in distilled water, the pH value of the solution was adjusted to 7 by potassium hydroxide and the resulting solution was administered. The test compound was administered to a group consisting of 9 rats, and in place of the test compound, a 5% aqueous solution of gum arabic free of the test compound was administered to a control group consisting of 14 rats. Neither the test compound nor D-galactosamine hydrochloride was administered to a normal group consisting of 9 rats.

Administration Schedule:

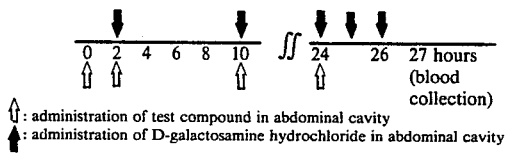

⇓: administration of test compound in abdominal cavity
⬇: administration of D-galactosamine hydrochloride in abdominal cavity

EXPERIMENT II

The effect on the liver dysfunction (hepatitis) induced by D-galactosamine by oral administration was examined.

D-galactosamine hydrochloride (200 mg/Kg each time) was hypodermically administered, and the test compound (400 mg/Kg each time) was orally administered. The test compound-administered group consisted of 9 rats, the control group consisted of 14 rats, and the normal group consisted of 8 rats. The administration schedule was as follows.

Administration Schedule:

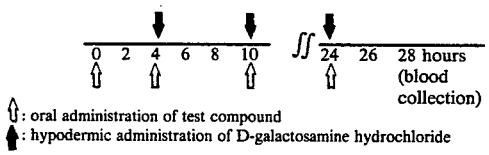

⇓: oral administration of test compound
⬇: hypodermic administration of D-galactosamine hydrochloride Other test conditions were the same as in Experiment I.

EXPERIMENTAL RESULTS

The obtained results are shown in Tables 1 to 4.

TABLE 1

| | Administration in Abdominal Cavity | | |
|---|---|---|---|
| | Test Items | | |
| Test Group | GPT Value (carmen unit) | GOT Value (carmen unit) | Alkali Phosphatase Value (KA unit) |
| Normal Group | 33.1 ± 2.3 | 127.0 ± 6.1 | 32.3 ± 3.3 |
| Control Group | 509 ± 94 | 751 ± 130 | 94.2 ± 6.9 |
| Test Compound-Administered Group | | | |
| compound A | 46.8 ± 11 | 257.4 ± 31 | 31.9 ± 1.8 |
| compound B | 50.4 ± 16 | 316 ± 27 | 40.2 ± 2.4 |
| compound C | 40 ± 13 | 352 ± 34 | 23.5 ± 1.8 |

TABLE 1-continued

| | Administration in Abdominal Cavity | | |
| --- | --- | --- | --- |
| | Test Items | | |
| Test Group | GPT Value (carmen unit) | GOT Value (carmen unit) | Alkali Phosphatase Value (KA unit) |
| compound D | 94 ± 39 | 430 ± 58 | 28.5 ± 2.0 |
| compound E | 64 ± 15 | 425 ± 24 | 32.1 ± 2.6 |
| compound F | 90 ± 44 | 400 ± 75 | 28.0 ± 2.4 |
| compound G | 84 ± 17 | 414 ± 49 | 29.6 ± 2.3 |

TABLE 2

| | Administration in Abdominal Cavity | | |
| --- | --- | --- | --- |
| | Test Items | | |
| Test Group | GPT Value (carmen unit) | GOT Value (carmen unit) | Alkali Phosphatase Value (KA unit) |
| Normal Group | 39.0 ± 2.4 | 129.9 ± 10.1 | 48.9 ± 4.7 |
| Control Group | 992.3 ± 121.2 | 1081.8 ± 90.3 | 125.7 ± 4.9 |
| Test Compound-Administered Group | | | |
| compound H | 511.3 ± 173.7 | 732.1 ± 147.3 | 49.0 ± 1.9 |
| compound I | 135.3 ± 46.4 | 659.3 ± 72.5 | 35.4 ± 5.2 |
| compound J | 314.5 ± 65.9 | 617.0 ± 50.5 | 49.9 ± 3.0 |
| compound K | 193.8 ± 38.1 | 586.0 ± 56.5 | 45.2 ± 1.8 |
| compound L | 138.1 ± 16.9 | 451.7 ± 37.9 | 42.8 ± 1.8 |

TABLE 3

| | Oral Administration | | |
| --- | --- | --- | --- |
| | Test Items | | |
| Test Groups | GPT Value (carmen unit) | GOT Value (carmen unit) | Alkali Phosphatase Value (KA unit) |
| Normal Group | 34.8 ± 1.9 | 129.4 ± 12.6 | 49.3 ± 4.4 |
| Control Group | 395.7 ± 49.3 | 573.7 ± 59.1 | 67.4 ± 2.9 |
| Test Compound-Administered Group | | | |
| compound A | 62.1 ± 10.7 | 193.0 ± 18.5 | 64.1 ± 4.6 |
| compound B | 67.4 ± 7.3 | 233.3 ± 22.2 | 62.9 ± 4.9 |
| compound C | 122.0 ± 16.1 | 231.1 ± 26.4 | 46.7 ± 4.0 |
| compound D | 58.8 ± 5.5 | 84.8 ± 8.9 | 53.1 ± 5.6 |

TABLE 4

| | Oral Administration | | |
| --- | --- | --- | --- |
| | Test Items | | |
| Test Groups | GPT Value (carmen unit) | GOT Value (carmen unit) | Alkali Phosphatase Value (KA unit) |
| Normal Group | 34.8 ± 1.9 | 129.4 ± 12.6 | 49.3 ± 4.4 |
| Control Group | 395.7 ± 49.3 | 573.7 ± 59.1 | 67.4 ± 2.9 |
| Test Compound-Administered Group | | | |
| compound I | 154.9 ± 21.5 | 284.9 ± 36.4 | 44.31 ± 3.1 |
| compound M | 58.9 ± 7.3 | 178.4 ± 10.3 | 59.4 ± 4.9 |

As will be apparent from the results shown in Tables 1 to 4, the GPT value, GOT value and alkali phosphatase value of each test compound-administered group are lower than those of the control group, and they are close to the values of the normal group. These results show that the liver dysfunction induced by administration of D-galactosamine hydrochloride can be moderated or prevented by administration of the compounds of the present invention.

TOXICITY

The compounds C, D, I and M were separately suspended in 5% aqueous solutions of gum arabic and the test composition were orally administered to rats of the Wistar series at a dose of 4000 mg/Kg. None of the rats died.

From the foregoing results, it will be readily understood that the compounds of the present invention have low toxicity and they can be used for treatment of liver dysfunction.

The compounds of the present invention can be administered either orally or non-orally, but oral administration is especially preferred. The daily dose for an adult is 50 to 2000 mg, preferably 200 to 600 mg. The compounds of the present invention can be administered in the form of a powder, a granule, a hard capsule, a tablet or a soft capsule. These unit dosage forms can be manufactured by using conventional carriers customarily used in the pharmaceutical industry.

The present invention will now be described in detail with reference to the following Examples.

EXAMPLE 1

This Example illustrates synthesis of (E,E)-3,7,11,15-tetramethyl-6,10,14-hexadecatrienamide (compound E).

(a) Synthesis of ethyl (E,E)-2-cyano-3,7,11,15-tetramethyl-6,10,14-hexadecatrienoate:

In 200 ml of benzene was dissolved 50 g of farnesylacetone, and 28 g of ethyl cyanoacetate, 5 g of ammonium acetate and 5 g of acetic acid were added to the solution. The mixture was refluxed for 8 hours while removing the water formed by the reaction. The liquid reaction mixture was washed with water and dried and a solution of 4.3 g of sodium borohydride in 50 ml of ethanol was added dropwise to the reaction mixture under agitation at 10° to 20° C. The resulting mixture was stirred for 1 hour. To the liquid reaction mixture was added 50 ml of 10% acetic acid, and the mixture was washed with water and dried. The solvent was removed by distillation and the residue was purified by column chromatography using silica gel to obtain 50.5 g of the intended compound on the form of an oil.

(B) Synthesis of (E,E)-3,7,11,15-tetramethyl-6,10,14-hexadecatrienonitrile:

To all of the compound obtained in step (A) above were added 29 g of sodium hydroxide and 100 ml of propylene glycol, and the mixture was stirred at room temperature for 10 minutes. The liquid reaction mixture was made acidic by addition of 6N hydrochloric acid and was extracted with benzene. The extract was washed with water and dried, and the solvent was removed by distillation. The obtained oily substance was dissolved in 100 ml of pyridine and 0.5 g of copper powder was added to the solution, and the mixture was refluxed for 2 hours. The copper powder was removed by filtration and the solvent was removed by distillation. The residue was dissolved in h-hexane and the solution was washed with water and dried. The solvent was removed by distillation and the residue was purified by column chromatography using silica gel to obtain 34 g of the intended compound in the form of an oil.

(c) Synthesis of (E,E)-3,7,11,15-tetramethyl-6,10,14-hexadecatrienoic acid:

To 34 g of the compound obtained in step (b) above were added 23 g of potassium hydroxide, 10 ml of water and 70 ml of propylene glycol, and the mixture was stirred at 130° C. for 7 hours. The liquid reaction mixture was made acidic with hydrochloric acid and was extracted with n-hexane. The extract was washed with water and dried, and the solvent was removed by distillation and the residue was purified by column chromatography using silica gel to obtain 30 g of the intended compound in the form of an oil.

(d) Synthesis of (E,E)-3,7,11,15-tetramethyl-6,10,14-hexadecatrienoic acid chloride:

At room temperature, 9.2 g of the compound obtained in step (c) above was dropped into a 55% benzene suspension containing 1.3 g of sodium hydroxide, and the mixture was stirred at 50° C. for 10 minutes. The liquid reaction mixture was cooled to room temperature, and 3.8 g of oxazolyl chloride was dropped into the liquid reaction mixture and the resulting mixture was stirred at 50° C. for 30 minutes. The liquid reaction mixture was filtered and the solvent was removed from the filtrate by distillation under reduced pressure at a temperature lower than 40° C. to obtain 9.5 g of the intended compound in the form of an oil.

(e) Synthesis of (E,E)-3,7,11,15-tetramethyl-6,10,14-hexadecatrienamide:

To 100 ml of a tetrahydrofuran solution containing 1 g of ammonia, 9.5 g of the compound obtained in step (d) above was added dropwise at 0° to 5° C., and the mixture was stirred at room temperature for 30 minutes. The liquid reaction mixture was extracted with n-hexane, and the extract was washed with water and dried. The solvent was removed by distillation and the obtained oily substance was purified by column chromatography using silica gel to obtain 5.6 g of the intended compound in the form of an oil.

Infrared absorption spectrum (cm$^{-1}$, neat): 3500, 3400, 1640.

Mass spectrum: 305 (M+).

Elementary analysis values as $C_{20}H_{35}ON$: Calculated: C=78.63%, H=11.55%, N=4.59%. Found: C=78.48%, H=11.51%, N=4.67%.

NMR spectrum (δ, CDCl$_3$): 0.99 (3H, d), 1.2–1.5 (3H, m), 1.64 (9H, s), 1.72 (3H, s), 1.9–2.2 (10H, m), 2.2 (2H, d), 5.0–5.2 (3H, m) 5.7 (1H, s), 6.3 (1H, s).

EXAMPLE 2

This Example illustrates the synthesis of (E,E)-N,N-dimethyl-3,7,11,15-tetramethyl-6,10,14-hexadecatrienamide (compound F).

To 100 ml of a tetrahydrofuran solution containing 3.5 g of dimethylamine, 9.7 g of the acid chloride obtained in step (d) of Example 1 was added dropwise at 0° to 5° C., and the mixture was treated in the same manner as described in step (e) of Example 1 to obtain 6.3 g of the intended compound in the form of an oil.

Infrared absorption spectrum (cm$^{-1}$, neat): 1640.

Mass spectrum: 333 (M+).

Elementary analysis values as $C_{22}H_{30}ON$: Calculated: C=79.22%, H=11.79%, N=4.20%. Found: C=79.04%, H=11.71%, N=4.32%.

NMR Spectrum (δ, CDCl$_3$): 0.99 (3H, d), 1.2–1.5 (3H, m), 1.64 (9H, s), 1.72 (3H, s), 1.92–2.2 (10H, m) 2.2 (2H, m), 2.98 (3H, s), 3.02 (3H, s), 5.0–5.2 (3H, m).

EXAMPLE 3

This Example illustrates the synthesis of 4-[(E,E)-3,7,11,15-tetramethyl-6,10,14-hexadecatrienoyl]morpholine (compound D).

In anhydrous tetrahydrofuran was dissolved 9.2 g of the compound obtained in step (c) of Example 1, and 3 g of triethylamine and then 3.3 g of ethyl chlorocarbonate were added to the solution at 0° C. and the mixture was stirred for 20 minutes. At 0° C., 3.1 g of morpholine was added dropwise to the liquid reaction mixture, and the resulting mixture was stirred for 30 minutes. The liquid reaction mixture was extracted with n-hexane, and the extract was washed with water and dried. The solvent was removed by distillation and the residue was purified by column chromatograph using silica gel to obtain 7.2 g of the intended compound in the form of an oil.

Infrared absorption spectrum (cm$^{-1}$, neat): 1640, 1100.

Mass spectrum: 375 (M+).

Elementary analysis values as $C_{24}H_{41}O_2N$: Calculated: C=76.75%, H=11.00%, N=3.73%. Found: C=76.62%, H=10.91%, N=3.80%.

NMR spectrum (δ, CDCl$_3$): 0.99 (3H, d), 1.2–1.5 (3H, m), 1.64 (9H, s), 1.72 (3H, s), 1.9–2.2 (10H, m), 2.2 (2H, d), 3.4–3.8 (8H, m), 5.0–5.2 (3H, m).

EXAMPLE 4

This Example illustrates the synthesis of 1-[(E,E)-3,7,11,15-tetramethyl-6,10,14-hexadecatrienoyl]-4-formylpiperazine.

To 100 ml of a benzene solution containing 5 g of 1-formylpiperazine and 3.6 g of triethylamine, 9.7 g of the acid chloride obtained in step (d) of Example 1 was added dropwise at 0° to 5° C., and the mixture was stirred at room temperature for 30 minutes. The liquid reaction mixture was treated in the same manner as described in step (e) of Example 1 to obtain 8.5 g of the intended compound in the form of an oil.

Infrared absorption spectrum (cm$^{-1}$, neat): 1680, 1640.

Mass spectrum: 402 (M+).

Elementary analysis values as $C_{25}H_{42}O_2N_2$: Calculated: C=74.58%, H=10.52%, N=6.96%. Found: C=74.41%, H=10.35%, N=7.07%.

NMR spectrum (δ, CDCl$_3$): 0.99 (3H, d), 1.2–1.5 (3H, m), 1.64 (9H, s), 1.72 (3H, s), 1.9–2.2 (10H, m), 2.2 (2H, d), 3.2–3.7 (8H, m), 5.0–5.2 (3H, m), 8.1 (1H, s).

EXAMPLE 5

This Example illustrates the synthesis of 1-[(E,E)-3,7,11,15-tetramethyl-6,10,14-hexadecatrienoyl]piperazine.

To 100 ml of anhydrous dimethylsulfoxide solution containing 0.9 g of 55% sodium hydroxide, there was added 8 g of the compound obtained in Example 4, and the mixture was stirred at 100° to 120° C. for 1 hour. The liquid reaction mixture was poured into ice water and extracted with n-hexane. The extract was washed with water and dried. The solvent was removed by distillation and the residue was purified by column chromatography using silica gel to obtain 4 g of the intended compound in the form of an oil.

Infrared absorption spectrum (cm$^{-1}$, neat): 3340, 1640.

Mass spectrum: 374 (M+).

Elementary analysis values as $C_{24}H_{42}ON_2$: Calculated: C=76.95%, H=11.30%, N=7.48% Found: C=76.70%, H=11.24%, N=7.59%.

NMR spectrum (δ, CDCl$_3$): 0.99 (3H, d), 1.2–1.5 (3H, m), 1.64 (9H, s), 1.72 (3H, s), 1.9–2.2 (10H, m), 2.2 (2H, d), 2.8–2.9 (4H, m), 3.4–3.7 (4H, m), 5.0–5.2 (3H, m).

EXAMPLE 6

This Example illustrates the synthesis of 1-[(E,E)-3,7,11,15-tetramethyl-6,10,14-hexadecatrienoyl]-4-(2-hydroxyethyl)piperazine (compound G).

At a temperature of −10° to −20° C., 13 g of the acid chloride obtained in step (d) of Example 1 was added dropwise to 100 ml of tetrahydrofuran solution containing 7.8 g of 1-piperazine-ethanol and 4 g of triethylamine, and the mixture was stirred at −10° C. for 1 hour and 30 minutes. The liquid reaction mixture was treated in the same manner as described in step (e) of Example 1 to obtain 8.5 g of the intended compound in the form of an oil.

Infrared absorption spectrum (cm$^{-1}$, neat): 3400, 1640.

Mass spectrum: 418 (M+).

Elementary analysis values as $C_{25}H_{46}O_2N_2$: Calculated: C=74.59%, H=11.08%, N=6.69%. Found: C=74.38%, H=11.12%, N=6.72%.

NMR spectrum (δ, CDCl$_3$): 0.99 (3H, d), 1.2–1.5 (3H, m), 1.64 (9H, s), 1.72 (3H, s), 1.9–2.2 (10H, m), 2.2 (2H, d), 2.4–2.6 (6H, m), 3.04 (1H, s), 3.4–3.7 (6H, m) 5.0–5.2 (3H, m).

EXAMPLE 7

This Example illustrates the synthesis of (E,E)-N-(2,6-dimethylphenyl)-3,7,11,15-tetramethyl-6,10,14-hexadecatrienamide.

By using 9.7 g of the acid chloride obtained in step (d) of Example 1, 3.6 g of xylidine and 3.6 g of triethylamine in benzene, the reaction and post treatment were carried out in the same manner as described in step (e) of Example 1 to obtain 6.5 g of the intended compound in the form of an oil.

Infrared absorption spectrum (cm$^{-1}$, neat): 3250, 1640.

Mass spectrum: 409 (M+).

Elementary analysis values as $C_{28}H_{43}ON$: Calculated: C=82.00%, H=10.58%, N=3.42%. Found: C=82.21%, H=10.44%, N=3.31%.

NMR spectrum (δ, CDCl$_3$): 0.99 (3H, d), 1.2–1.5 (3H, m), 1.64 (9H, s), 1.72 (3H, s), 1.9–2.2 (10H, m), 2.2 (2H, d), 2.2 (6H, s), 5.0–5.2 (3H, m), 7.02 (3H, s), 7.5 (1H, s).

EXAMPLE 8

This Example illustrates the synthesis of 4-(3,7,11,15-tetramethylhexadecanoyl)morpholine (compound C).

(a) Synthesis of 4-(3,7,11,15-tetramethyl-2,6,10,14-hexadecatetraenoyl)morpholine (compound M):

To a suspension of 5 g of 55% sodium hydroxide in 200 ml of anhydrous tetrahydrofuran was dropped 22 g of diethylphosphonoacetomorpholide, and 16.8 g of farnesylacetone was added to the mixture. The resulting mixture was stirred at 50° C. for 2 hours. Water was added to the liquid reaction mixture and the resulting mixture was extracted with n-hexane. The extract was washed with water and dried, and the solvent was removed by distillation and the residue was purified by column chromatography using silica gel to obtain 18 g of the intended compound [mixture of (E,E,E) and (Z,E,E)] in the form of an oil.

Infrared absorption spectrum (cm$^{-1}$, nujol): 1640, 1100.

Mass spectrum: 373 (M+).

Elementary analysis values as $C_{24}H_{39}O_2N$: Calculated: C=77.16%, H=10.52%, N=3.75%. Found: C=77.04%, H=10.47%, N=3.91%.

NMR spectrum (δ, CDCl$_3$): 1.64 (9H, s), 1.72 (3H, s), 1.92 (3H, s), 2.0–2.2 (12H, m), 3.4–3.8 (8H, m), 5.0–5.2 (3H, m), 5.8 (1H, s).

(b) Synthesis of 4-(3,7,11,15-tetramethylhexadecanoyl)morpholine:

In 100 ml of dioxane was dissolved 10 g of the compound obtained in step (a) above, and 1 g of 10% palladium-carbon was added to the solution. Reaction was carried out in an autoclave under a hydrogen gas pressure of 10 atmospheres at room temperature for 3 hours. The liquid reaction mixture was filtered, and the solvent was removed from the filtrate by distillation. The residue was purified by column chromatography using silica gel to obtain 9 g of the intended compound in the form of an oil.

Infrared absorption spectrum (cm$^{-1}$, neat): 1640, 1100.

Mass spectrum: 381 (M+).

Elementary analysis values as $C_{24}H_{47}O_2N$: Calculated: C=75.53%, H=12.41%, N=3.67%. Found: C=75.41%, H=12.55%, N=3.72%.

NMR spectrum (δ, CDCl$_3$): 0.9–1.0 (15H, m), 1.0–1.8 (22H, m) 2.2 (2H, d), 3.4–3.7 (8H, m).

EXAMPLE 9

This Example illustrates the synthesis of 4-[(E,E)-3,7,11,15-tetramethyl-6,10,14-hexadecartrienoyl]morpholine (compound D).

In 100 ml of methanol was dissolved 10 g of the compound obtained in step (a) of Example 8, and 0.7 g of nickel chloride and 2 g of sodium borohydride were added to the solution. The mixture was stirred at room temperature for 2 hours, and the liquid reaction mixture was extracted with n-hexane, and the extract was washed with water and dried. The solvent was removed by distillation, and the residue was purified by column chromatography using silica gel to obtain 9.5 g of the intended compound in the form of an oil.

Infrared absorption spectrum (cm$^{-1}$, neat): 1640, 1100.

Mass spectrum: 375 (M+).

Elementary analysis values as $C_{24}H_{41}O_2N$: Calculated: C=76.75%, H=11.00%, N=3.73%. Found: C=76.58%, H=10.96%, N=3.75%.

NMR spectrum (δ, CDCl$_3$) 0.99 (3H, d), 1.2–1.5 (3H, m), 1.64 (9H, s), 1.72 (3H, s), 1.9–2.2 (10H, m), 2.2 (2H, d), 3.4–3.8 (8H, m), 5.0–5.2 (3H, m).

EXAMPLE 10

This Example illustrates the synthesis of 4-[(E)-3,7,11-trimethyl-6,10-dodecadienoyl]morpholine (compound B).

(a) Synthesis of ethyl (E)-2-cyano-3,7,11-trimethyl-6,10-dodecadienoate:

In 200 ml of benzene was dissolved 50 g of geranylacetone, and 42 g of ethyl cyanoacetate, and then 6 g of ammonium acetate and 6 g of acetic acid were added to the solution. The mixture was refluxed for 8 hours while removing the water formed by the reaction. This liquid reaction mixture was washed with water and dried, and a solution of 5.7 g of sodium borohydride in 40 ml of ethanol was added dropwise to the liquid reaction mixture at 10° to 20° C. under agitation. The mixture was stirred for 1 hour and 60 ml of 10% acetic acid was added to the liquid reaction mixture. Then, the mixture was washed with water and dried, and the solvent was removed by distillation and the residue was purified by column chromatography using silica gel to obtain 59 g of the intended compound in the form of an oil.

(b) Synthesis of (E)-3,7,11-trimethyl-6,10-dodecadienonitrile:

To all of the compound obtained in step (a) above were added 39 g of sodium hydroxide and 120 ml of propylene glycol, and the mixture was stirred at room temperature for 10 minutes. The liquid reaction mixture was made acidic by addition of 6N hydrochloric acid and was extracted with benzene. The extract was washed with water and dried, and the solvent was removed by distillation. The residue was dissolved in 120 ml of pyridine and 0.6 g of copper powder was added to the solution. The mixture was refluxed for 2 hours, and the copper powder was removed by filtration and the solvent was removed by distillation. The residue was dissolved in n-hexane, and the solution was washed with water and dried. The solvent was removed by distillation and the residue was purified by column chromatography using silica gel to obtain 45 g of the intended compound in the form of an oil.

(c) Synthesis of (E)-3,7,11-trimethyl-6,10-dodecadienoic acid:

To 40 g of the compound obtained in step (b) above were added 35 g of potassium hydroxide, 15 ml of water and 80 ml of propylene glycol, and the mixture was stirred at 130° C. for 7 hours. The extract was washed with water and dried, then the solvent was removed by distillation and then the residue was purified by column chromatography using silica gel to obtain 36 g of the intended compound in the form of an oil.

(d) Synthesis of 4-[(E)-3,7,11-trimethyl-6,10-dodecadienoyl]-morpholine:

In anhydrous tetrahydrofuran was dissolved 6.9 g of the compound obtained in step (c) above, and 3 g of triethylamine and then 3.3 g of ethyl chlorocarbonate were added to the solution at 0° C. The mixture was stirred for 20 minutes. Into the liquid reaction mixture was dropped 3.1 g of morpholine at 0° C., and the mixture was stirred for 30 minutes. The liquid reaction mixture was extracted with n-hexane, and the extract was washed with water and dried. The solvent was removed by distillation and the residue was purified by column chromatography using silica gel to obtain 5.6 g of the intended compound in the form of an oil.

Infrared absorption spectrum (cm$^{-1}$), neat): 1640, 1100.

Mass spectrum: 307 (M+).

Elementary analysis values as $C_{19}H_{33}O_2N$: Calculated: C=74.22%, H=10.81%, N=4.56%. Found: C=74.19%, H=10.70%, N=4.61%.

NMR spectrum (δ, CDCl$_3$): 0.99 (3H, d), 1.2–1.5 (3H, m), 1.64 (6H, s), 1.72 (3H, s), 1.9–2.2 (6H, m), 2.2 (2H, d), 3.4–3.8 (8H, m), 5.0–5.2 (2H, m).

The compounds of Examples 11 to 58 were synthesized according to the same methods as described in Examples 1 to 10. The obtained compounds are shown in Table 5. In Table 5, the preparation process A and C mean the processes A and C described hereinbefore. Furthermore, in Table 5, the symbol "————" in column "a,b" indicates that a and b together define a direct valence bond between the carbon atoms to which they are attached.

TABLE 5

$$H+CH_2-\underset{\underset{a}{|}}{\overset{\overset{CH_3}{|}}{C}}-\underset{\underset{b}{|}}{CH}-CH_2\overline{)_n}CH_2-\overset{\overset{CH_3}{|}}{CH}-CH_2-CON\diagdown_{R_2}^{R_1}$$

| Example No. | Preparation Process | n | a | b | −N⟨R₁/R₂ | Molecular Formula and State | Elementary Analysis Values calculated (%) / found (%) C | H | N | Mass spectrum (M+) | NMR spectrum (δ, CDCl₃) |
|---|---|---|---|---|---|---|---|---|---|---|---|
| 11 | A | 1 | — | — | —NH₂ | C₁₀H₁₉ON, oil | 70.96 / 70.82 | 11.32 / 11.23 | 8.28 / 8.12 | 169 | 0.99(3H,d), 1.2–1.5(3H,m), 1.64(3H,s), 1.72(3H,s), 1.9–2.2(2H,m), 22(2H,d), 5.0–5.2(1H,m), 5.7(1H,s), 6.3(1H,s) |
| 12 | A | 1 | — | — | —NHCH₃ | C₁₁H₂₁ON, oil | 72.08 / 72.19 | 11.55 / 11.63 | 7.64 / 7.71 | 183 | 0.99(3H,d), 1.2–1.5(3H,m), 1.64(3H,s), 1.72(3H,s), 1.9–2.2(2H,m), 22(2H,d), 30(3H,s), 5.0–5.2(1H,m), 5.5(1H,s) |
| 13 | A | 1 | — | — | —N(CH₃)₂ | C₁₂H₂₃ON, oil | 73.04 / 73.18 | 11.75 / 11.60 | 7.10 / 7.21 | 197 | 0.99(3H,d), 1.2–1.5(3H,m), 1.64(3H,s), 1.72(3H,s), 1.9–2.2(2H,m), 2.2(2H,d), 2.98(3H,s), 3.02(3H,s), 5.0–5.2(1H,m) |
| 14 | A | 1 | — | — | —N(pyrrolidinyl) | C₁₄H₂₅ON, oil | 75.28 / 75.11 | 11.28 / 11.13 | 6.27 / 6.40 | 223 | 0.99(3H,d), 1.2–1.5(3H,m), 1.4–2.7(4H,m), 1.64(3H,s), 1.72(3H,s), 1.9–2.2(2H,d), 2.2(2H,d), 3.2–4.7(4H,m), 5.0–5.2(1H,m) |
| 15 | A | 1 | — | — | —N(piperidinyl) | C₁₅H₂₇ON, oil | 75.89 / 75.99 | 11.47 / 11.39 | 5.90 / 5.97 | 237 | 0.99(3H,d), 1.2–1.5 (3H,m), 1.4–2.7(6H,m), 1.64(3H,s),1.72(3H,s), 1.9–2.2(2H,m), 2.2 (2H,d), 3.2–4.7(4H,m), 5.0–5.2(1H,m) |

TABLE 5-continued $$H\text{-}(CH_2\text{-}\underset{a}{\underset{|}{\overset{CH_3}{\overset{|}{C}}}}\text{-}\underset{b}{CH}\text{-}CH_2)_n\text{-}CH_2\text{-}\underset{|}{\overset{CH_3}{\overset{|}{CH}}}\text{-}CH_2\text{-}CON\underset{R_2}{\overset{R_1}{\diagdown}}$$

| Example No. | Preparation Process | n | a | b | −N(R₁)(R₂) | Molecular Formula and State | C calc/found | H calc/found | N calc/found | Mass spectrum (M⁺) | NMR spectrum (δ, CDCl₃) |
|---|---|---|---|---|---|---|---|---|---|---|---|
| 16 | A | 1 | — | — | −N(morpholino) | $C_{14}H_{25}O_2N$, oil | 70.25 / 70.12 | 10.53 / 10.39 | 5.85 / 5.69 | 239 | 0.99(3H,d), 1.2–1.5 (3H,m), 1.64(3H,s), 1.72(3H,s), 1.9–2.2 (2H,m) 2.2(2H,d), 3.4–3.8(8H,m), 5.0–5.2 (1H,m) |
| 17 | A | 1 | — | — | −N(piperazinyl)N−CHO | $C_{15}H_{26}O_2N_2$, oil | 67.63 / 67.80 | 9.84 / 9.92 | 10.52 / 10.38 | 266 | 0.99(3H,d), 1.2–1.5 (3H,m), 1.64(3H,s), 1.72(3H,s), 1.9–2.2 (2H,m), 2.2(2H,d), 3.2–3.7(8H,m), 5.0–5.2 (1H,m), 8.1(1H,s) |
| 18 | A | 1 | | | −N(piperazinyl)NH | $C_{14}H_{26}ON_2$, oil | 70.54 / 70.42 | 10.99 / 10.81 | 11.75 / 11.91 | 273 | 0.99(3H,d), 1.2–1.5 (3H,m), 1.64(3H,s), 1.72(3H,s), 1.9–2.2 (2H,m), 2.2(2H,d), 2.8–2.9(4H,m), 3.4–3.7 (4H,m), 5.0–5.2(1H,m) |
| 19 | A | 1 | — | — | −N(piperazinyl)N−(CH₂)₂−OH | $C_{16}H_{30}O_2N_2$, oil | 68.04 / 68.12 | 10.71 / 10.68 | 9.97 / 9.98 | 282 | 0.99(3H,d), 1.2–1.5 (3H,m), 1.64(3H,s), 1.72(3H,s), 1.9–2.2 (2H,m), 2.2(2H,d), 2.4–2.6(6H,m), 3.04 (1H,s), 3.4–3.7(6H,m), 5.0–5.2(1H,m) |
| 20 | A | 1 | — | — | −NH-(2,6-dimethylphenyl) | $C_{16}H_{27}ON$, oil | 79.07 / 79.23 | 9.95 / 9.79 | 5.12 / 5.27 | 273 | 0.99(3H,d), 1.2–1.5 (3H,m), 1.64(3H,s), 1.72(3H,s), 1.9–2.2 (2H,m), 2.2(2H,d), 2.2(6H,s), 5.05–5.2(1H,m), 7.02(3H,s), 7.5(1H,s) |
| 21 | A | 1 | — | — | −NHCH₂-(3,4-methylenedioxyphenyl) | $C_{18}H_{25}O_2N$, oil | 71.25 / 71.13 | 8.31 / 8.50 | 4.62 / 4.71 | 303 | 0.99(3H,d), 1.2–1.5 (3H,m), 1.64(3H,s), 1.72(3H,m), 1.64(3H,s), 1.72(3H,s), 1.9–2.2 (2H,m), 2.2(2H,d), 3.4(2H,s), 4.8(2H,d), 5.0–5.2(1H,m), 5.5(1H,s), 6.7(2H,s), 6.8(1H,s) |
| 22 | A | 2 | — | — | −NH₂ | $C_{15}H_{27}ON$, oil | 75.89 / 75.72 | 11.47 / 11.39 | 5.90 / 5.98 | 237 | 0.99(3H,d), 1.2–1.5 (3H,m), 1.64(6H,s), 1.72(3H,s), 1.9–2.2 (6H,m), 2.2(2H,d), 5.0–5.2(2H,m), 5.7(1H,s), 6.3(1H,s) |
| 23 | A | 2 | — | — | −NHCH₃ | $C_{16}H_{29}ON$, oil | 76.44 / 76.67 | 11.63 / 11.51 | 5.57 / 5.68 | 251 | 0.99(3H,d), 1.2–1.5 (3H,m), 1.64(6H,s), 1.72(3H,s), 1.9–2.2 (6H,m), 2.2(2H,d), 3.0(3H,s), 5.0–5.2 (2H,m), 5.5(1H,s) |
| 24 | A | 2 | — | — | −N(CH₃)₂ | $C_{17}H_{31}ON$, oil | 76.92 / 76.78 | 11.77 / 11.71 | 6.03 / 6.12 | 265 | 0.99(3H,d), 1.2–1.5 (3H,m),1.64(6H,s), 1.72(3H,s), 1.9–2.2 (6H,m), 2.2(2H,d), 2.98(3H,s), 3.02(3H,s), 5.0–5.2(2H,m) |

TABLE 5-continued $$H\text{-}(CH_2\text{-}\underset{\underset{a}{|}}{\overset{\overset{CH_3}{|}}{C}}\text{-}\underset{\underset{b}{|}}{CH}\text{-}CH_2)_{\overline{n}}CH_2\text{-}\overset{\overset{CH_3}{|}}{CH}\text{-}CH_2\text{-}CON\overset{R_1}{\underset{R_2}{\diagdown}}$$

| Example No. | Preparation Process | n | a | b | $-N\diagdown_{R_2}^{R_1}$ | Molecular Formula and State | Elementary Analysis Values $\binom{\text{calculated (\%)}}{\text{found (\%)}}$ C | H | N | Mass spectrum (M+) | NMR spectrum (δ, CDCl$_3$) |
|---|---|---|---|---|---|---|---|---|---|---|---|
| 25 | A | 2 | — | — | pyrrolidinyl | $C_{19}H_{33}ON$, oil | 78.29 / 78.40 | 11.41 / 11.28 | 4.81 / 4.70 | 291 | 0.99(3H,d), 1.2–1.5 (3H,m), 1.4–2.7(4H,m), 1.64(6H,s), 1.72(3H,s), 1.9–2.2(6H,m), 2.2 (2H,d), 3.2–4.7(4H,m), 5.0–5.2(2H,m) |
| 26 | A | 2 | — | — | piperidinyl | $C_{20}H_{35}ON$, oil | 78.63 / 78.59 | 11.55 / 11.47 | 4.59 / 4.66 | 305 | 0.99(3H,d), 1.2–1.5 (3H,m), 1.4–2.7(6H,m), 1.64(6H,s), 1.72(3H,s), 1.9–2.2(6H,m),2.2 (2H,d), 3.2–4.7(4H,m), 5.0–5.2(2H,m) |
| 27 | A | 2 | — | — | 4-formylpiperazinyl | $C_{20}H_{34}O_2N_2$, oil | 71.81 / 71.64 | 10.25 / 10.12 | 8.38 / 8.51 | 334 | 0.99(3H,d), 1.2–1.5(3H,m), 1.64(6H,s), 1.72(3H,s), 1.9–2.2(6H,m), 2.2(2H,d), 3.2–3.7(8H,m), 5.0–5.2 (2H,m), 8.1(1H,s) |
| 28 | A | 2 | — | — | piperazinyl | $C_{19}H_{24}ON_2$, oil | 74.46 / 74.31 | 11.18 / 11.07 | 9.14 / 9.23 | 306 | 0.99(3H,d), 1.2–1.5(3H,m), 1.64(6H,s), 1.72(3H,s), 1.9–2.2(6H,m), 2.2(2H,d), 2.8–2.9(4H,m),3.4–3.7 (4H,m), 5.0–5.2(2H,m) |
| 29 | A | 2 | — | — | 4-(2-hydroxyethyl)piperazinyl | $C_{21}H_{38}O_2N_2$, oil | 71.95 / 71.72 | 10.93 / 10.78 | 7.99 / 8.12 | 350 | 0.99(3H,d), 1.2–1.5(3H,m), 1.64(6H,s), 1.72(3H,s), 1.9–2.2(6H,d), 2.4–2.6 (6H,m), 3.05(1H,s), 3.4–3.7(6H,m), 5.0–5.2 (2H,m) |
| 30 | A | 2 | — | — | 2,6-dimethylanilino | $C_{23}H_{35}ON$, oil | 80.88 / 80.69 | 10.33 / 10.24 | 4.10 / 4.23 | 341 | 0.99(3H,d), 1.2–1.5(3H,m), 1.64(6H,s), 1.72(3H,s), 1.9–2.2(6H,m), 2.2(2H,d), 2.2(6H,s), 5.0–5.2(2H,m), 7.02(3H,s), 7.5(1H,s) |
| 31 | A | 2 | — | — | piperonylamino | $C_{23}H_{33}O_2N$, oil | 74.39 / 74.52 | 8.95 / 8.90 | 3.77 / 3.71 | 371 | 0.99(3H,d), 1.2–1.5(3H,m), 1.64(6H,s), 1.72(3H,s), 1.9–2.2(6H,m), 2.2(2H,d), 3.4(2H,s), 4.8(2H,d), 5.0–5.2(2H,m),5.5(1H,s), 6.7(2H,s), 6.8(1H,s) |
| 32 | A | 3 | — | — | —NHCH$_3$ | $C_{21}H_{37}ON$, oil | 78.94 / 78.77 | 11.67 / 11.69 | 4.38 / 4.45 | 319 | 0.99(3H,d), 1.2–1.5(3H,m), 1.64(9H,s), 1.72(3H,s), 1.9–2.2(10H,m), 2.2(2H,d), 3.0(3H,s), 5.0–5.2(3H,m), 5.5(1H,s) |
| 33 | A | 3 | — | — | piperidinyl | $C_{24}H_{41}ON$, oil | 80.15 / 80.27 | 11.49 / 11.35 | 3.90 / 3.84 | 359 | 0.99(3H,d), 1.2–1.5(3H,m), 1.4–2.7(4H,m), 1.64(9H,s), 1.72(3H,s), 1.9–2.2(10H,m), 2.2(2H,d), 3.2–4.7(4H,m), 5.0–5.2(3H,m) |
| 34 | A | 3 | — | — | hexahydroazepinyl | $C_{25}H_{43}ON$, oil | 80.37 / 80.44 | 11.60 / 11.52 | 3.75 / 3.75 | 373 | 0.99(3H,d), 1.2–1.5(3H,m), 1.3–2.7(6H,m), 1.64(9H,s), 1.72(3H,s), 1.9–2.2(10H,m), 2.2(2H,d), 3.2–4.7(4H,m), 5.0–5.2(1H,m) |

TABLE 5-continued $$H{+}CH_2-\underset{\underset{a}{|}}{\overset{\overset{CH_3}{|}}{C}}-\underset{\underset{b}{|}}{CH}-CH_2{)_n}CH_2-\overset{\overset{CH_3}{|}}{CH}-CH_2-CO\underset{R_2}{\overset{R_1}{N}}$$

| Example No. | Preparation Process | n a b | $-N\begin{smallmatrix}R_1\\R_2\end{smallmatrix}$ | Molecular Formula and State | Elementary Analysis Values calculated (%) / found (%) C | H | N | Mass spectrum (M+) | NMR spectrum (δ, CDCl₃) |
|---|---|---|---|---|---|---|---|---|---|
| 35 | A | 3 — — | —NHCH₂-(methylenedioxyphenyl) | $C_{27}H_{41}O_3N$, oil | 76.49 / 76.54 | 9.40 / 9.51 | 3.19 / 3.11 | 439 | 0.99(3H,d), 1.2-1.5(3H,m), 1.64(9H,s), 1.72(3H,s), 1.9-2.2(10H,m), 2.2(2H,d), 3.4(2H,d), 4.8(2H,d), 5.0-5.2(3H,m), 5.5(1H,s), 6.7(2H,s), 6.8(1H,s) |
| 36 | A | 4 — — | —NH₂ | $C_{25}H_{43}ON$, oil | 80.37 / 80.21 | 11.60 / 11.51 | 3.75 / 3.83 | 373 | 0.99(3H,d), 1.2-1.5(3H,m), 1.64(12H,s), 1.72(3H,s), 1.9-2.0(14H,m), 2.2(2H,d), 5.0-5.2(4H,m), 5.7(1H,s), 6.3(1H,s) |
| 37 | A | 4 — — | —NHCH₃ | $C_{26}H_{45}ON$, oil | 80.56 / 80.41 | 11.70 / 11.83 | 3.61 / 3.70 | 387 | 0.99(3H,d), 1.2-1.5(3H,m), 1.64(12H,s), 1.72(3H,s), 1.9-2.0(14H,m), 2.2(2H,d), 3.0(3H,s), 5.0-5.2(4H,s), 5.5(1H,s) |
| 38 | A | 4 — — | —N(CH₃)₂ | $C_{27}H_{47}ON$, oil | 80.73 / 80.88 | 11.80 / 11.87 | 3.49 / 3.40 | 401 | 0.99(3H,d), 1.2-1.5(3H,m), 1.64(12H,s), 1.72(3H,s), 1.9-2.0(14H,m), 2.2(2H,d), 2.98(3H,s), 3.02(3H,s), 5.0-5.2(4H,s) |
| 39 | A | 4 — — | —N(piperidino) | $C_{29}H_{49}ON$, oil | 81.44 / 81.31 | 11.55 / 11.49 | 3.28 / 3.35 | 427 | 0.99(3H,d), 1.2-1.5(3H,m), 1.4-2.7(4H,m), 1.64(12H,s), 1.72(3H,s), 1.9-2.0(14H,m), 2.2(2H,d), 3.2-4.7(4H,m), 5.0-5.2(4H,s) |
| 40 | A | 4 — — | —N(hexamethyleneimino) | $C_{30}H_{51}ON$, oil | 81.57 / 81.50 | 11.64 / 11.72 | 3.17 / 3.21 | 441 | 0.99(3H,d), 1.2-1.5(3H,m), 1.4-2.7(6H,m), 1.64(12H,s), 1.72(3H,s), 1.9-2.0(14H,m), 2.2(2H,d), 3.2-4.7(4H,m), 5.0-5.2(4H,s) |
| 41 | A | 4 — — | —N(morpholino) | $C_{29}H_{49}O_2N$, oil | 78.50 / 78.50 | 11.13 / 11.15 | 3.16 / 3.06 | 443 | 0.99(3H,d), 1.2-1.5(3H,m), 1.64(12H,s), 1.72(3H,s), 1.9-2.0(14H,m), 2.2(2H,d), 3.4-3.8(8H,m), 5.0-5.2(4H,s) |
| 42 | A | 4 — — | —N(piperazinyl-N'—CHO) | $C_{30}H_{50}O_2N_2$, oil | 76.54 / 76.21 | 10.71 / 10.64 | 5.95 / 6.10 | 470 | 0.99(3H,d), 1.2-1.5(3H,m), 1.64(12H,s), 1.72(3H,s), 1.9-2.2(14H,m), 2.2(2H,d), 3.2-3.7(8H,m), 5.0-5.2(4H,m), 8.1(1H,s) |
| 43 | A | 4 — — | —N(piperazinyl-NH) | $C_{29}H_{50}ON_2$, oil | 78.67 / 78.50 | 11.38 / 11.42 | 6.33 / 6.43 | 442 | 0.99(3H,d), 1.2-1.5(3H,m), 1.64(12H,s), 1.72(3H,s), 1.9-2.0(14H,m), 2.2(2H,d), 2.8-2.9(4H,m), 3.4-3.7(4H,m), 5.0-5.2(4H,s) |
| 44 | A | 4 — — | —N(piperazinyl-N'—(CH₂)₂—OH) | $C_{31}H_{54}O_2N_2$, oil | 74.59 / 74.38 | 11.08 / 11.12 | 6.69 / 6.72 | 418 | 0.99(3H,d), 1.2-1.5(3H,m), 1.64(12H,s), 1.72(3H,s), 1.9-2.0(14H,m), 2.2(2H,d), 2.4-2.6(6H,m), 3.04(1H,s), 3.4-3.7(6H,m), 5.0-5.2(4H,s) |
| 45 | A | 4 — — | —NH-(2,6-dimethylphenyl) | $C_{33}H_{51}ON$, oil | 82.00 / 82.21 | 10.58 / 10.44 | 3.42 / 3.31 | 409 | 0.99(3H,d), 1.2-1.5(3H,m), 1.64(12H,s), 1.72(3H,s), 1.9-2.0(14H,m), 2.2(2H,d), 2.2(6H,s), 5.0-5.2(4H,s), 7.02(3H,s), 7.5(1H,s) |

TABLE 5-continued $$H-(CH_2-\underset{\underset{a}{|}}{\overset{\overset{CH_3}{|}}{C}}-\underset{\underset{b}{|}}{CH}-CH_2)_{\overline{n}}CH_2-\overset{\overset{CH_3}{|}}{CH}-CH_2-CON\overset{R_1}{\underset{R_2}{\diagdown}}$$

| Example No. | Preparation Process | n a b | $-N\overset{R_1}{\underset{R_2}{\diagdown}}$ | Molecular Formula and State | Elementary Analysis Values $\left(\dfrac{\text{calculated (\%)}}{\text{found (\%)}}\right)$ C | H | N | Mass spectrum ($M^+$) | NMR spectrum ($\delta$, CDCl$_3$) |
|---|---|---|---|---|---|---|---|---|---|
| 46 | A | 4 — — | —NHCH$_2$–(3,4-methylenedioxyphenyl) | C$_{33}$H$_{49}$O$_3$N, oil | $\dfrac{76.49}{76.54}$ | $\dfrac{9.40}{9.51}$ | $\dfrac{3.19}{3.11}$ | 439 | 0.99(3H,d), 1.2–1.5(3H,m), 1.64(12H,s), 1.72(3H,s), 1.9–2.0(14H,m), 2.2(2H,s), 3.4(2H,s), 4.8(2H,d), 5.0–5.2(4H,s), 5.5(1H,s), 6.7(2H,s), 6.8(1H,s) |
| 47 | C | 1 H H | —NH$_2$ | C$_{10}$H$_{21}$ON, oil | $\dfrac{70.12}{70.01}$ | $\dfrac{12.36}{12.29}$ | $\dfrac{8.18}{8.23}$ | 171 | 0.9–1.0(9H,m), 1.0–1.8(8H,m), 2.2(2H,d), 5.7(1H,s), 6.3(1H,s) |
| 48 | C | 1 H H | morpholino | C$_{14}$H$_{27}$O$_2$N, oil | $\dfrac{69.66}{69.51}$ | $\dfrac{11.28}{11.12}$ | $\dfrac{5.80}{5.94}$ | 241 | 0.9–1.0(9H,m), 1.0–1.8(8H,m), 2.2(2H,d), 3.4–3.7(8H,m) |
| 49 | C | 1 H H | —NH-(2,6-dimethylphenyl) | C$_{18}$H$_{29}$ON, oil | $\dfrac{78.49}{78.55}$ | $\dfrac{10.61}{10.54}$ | $\dfrac{5.09}{5.18}$ | 275 | 0.9–1.0(9H,m), 1.0–1.8(8H,m), 2.2(2H,d), 2.2(6H,s), 7.02(3H,s), 7.5(1H,s) |
| 50 | C | 2 H H | —NH$_2$ | C$_{15}$H$_{31}$ON, oil | $\dfrac{74.63}{74.50}$ | $\dfrac{12.94}{13.11}$ | $\dfrac{5.80}{5.92}$ | 241 | 0.9–1.0(12H,m), 1.0–1.8 (15H,m), 2.2(2H,d), 5.7(1H,s), 6.3(1H,s) |
| 51 | C | 2 H H | morpholino | C$_{19}$H$_{37}$O$_2$N, oil | $\dfrac{73.26}{73.10}$ | $\dfrac{11.97}{11.89}$ | $\dfrac{4.50}{4.62}$ | 311 | 0.9–1.0(12H,m), 1.0–1.8 (15H,m), 2.2(2H,d), 3.4–3.7(8H,m) |
| 52 | C | 2 H H | —NH-(2,6-dimethylphenyl) | C$_{23}$H$_{39}$ON, oil | $\dfrac{79.94}{80.10}$ | $\dfrac{11.38}{11.24}$ | $\dfrac{4.05}{4.01}$ | 345 | 0.9–1.0(12H,m), 1.0–1.8 (15H,m), 2.2(2H,d), 2.2(6H,s), 7.02(3H,s), 7.5(1H,s) |
| 53 | C | 3 H H | —NH$_2$ | C$_{20}$H$_{41}$ON, oil | $\dfrac{77.10}{77.02}$ | $\dfrac{13.27}{13.39}$ | $\dfrac{4.50}{4.61}$ | 311 | 0.9–1.0(15H,m), 1.0–1.8 (22H,m), 2.2(2H,d), 5.7(1H,s), 6.3(1H,s) |
| 54 | C | 3 H H | morpholino | C$_{24}$H$_{47}$O$_2$N, oil | $\dfrac{75.53}{75.41}$ | $\dfrac{12.41}{12.55}$ | $\dfrac{3.67}{3.72}$ | 381 | 0.9–1.0(15H,m), 1.0–1.8 (22H,m), 2.2(2H,d), 3.4–3.7(8H,m) |
| 55 | C | 3 H H | —NH-(2,6-dimethylphenyl) | C$_{28}$H$_{49}$ON, oil | $\dfrac{80.90}{81.05}$ | $\dfrac{11.88}{11.79}$ | $\dfrac{3.37}{3.27}$ | 415 | 0.9–1.0(15H,m), 1.0–1.8 (22H,m), 2.2(2H,d), 2.2(6H,s), 7.02(3H,s), 7.5(1H,s) |
| 56 | C | 4 H H | —NH$_2$ | C$_{25}$H$_{51}$ON, oil | $\dfrac{78.67}{78.77}$ | $\dfrac{13.47}{13.36}$ | $\dfrac{3.67}{3.60}$ | 381 | 0.9–1.0(18H,m), 1.0–1.8 (29H,m), 2.2(2H,d), 5.7(1H,s), 6.3(1H,s) |

TABLE 5-continued $$H{-}(CH_2{-}\underset{a}{\underset{|}{C}}(CH_3){-}\underset{b}{\underset{|}{CH}}{-}CH_2)_{\overline{n}}CH_2{-}CH(CH_3){-}CH_2{-}CON\underset{R_2}{\overset{R_1}{\diagdown}}$$

| Example No. | Preparation Process | n | a | b | -N(R₁)(R₂) | Molecular Formula and State | Elementary Analysis Values calculated (%) / found (%) C | H | N | Mass spectrum (M+) | NMR spectrum (δ, CDCl₃) |
|---|---|---|---|---|---|---|---|---|---|---|---|
| 57 | C | 4 | H | H | 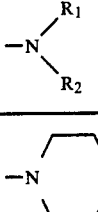 | $C_{29}H_{57}O_2N$, oil | 77.10 / 77.23 | 12.72 / 12.63 | 3.10 / 3.02 | 451 | 0.9–1.0(18H,m), 1.0–1.8 (29H,m), 2.2(2H,d), 3.4–3.7(8H,m) |
| 58 | C | 4 | H | H | 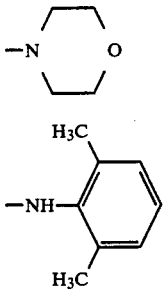 | $C_{33}H_{59}ON$, oil | 81.58 / 81.69 | 12.24 / 12.39 | 2.88 / 2.70 | 485 | 0.9–1.0(18H,m), 1.0–1.8 (29H,m), 2.2(2H,d), 2.2(6H,s), 7.02(3H,s), 7.5(1H,s) |

EXAMPLE 59

This Example illustrates the synthesis of 3,7,11,15-tetramethyl-2,6,10,14-hexadecatetraenamide (compound J).

In 100 ml of anhydrous tetrahydrofuran was suspended 5 g of 55% sodium hydride, and 25 g of diethylphosphonoacetamide was added to the suspension. Then, 16.8 g of farnesylacetone was further added, and the mixture was stirred at 50° C. for 2 hours. To the liquid reaction mixture was added 100 ml of water, and the mixture was extracted with n-hexane. The extract was washed with water and dried, and the solvent was removed by distillation and the residue was purified by column chromatography using silica gel to obtain 7 g of the intended compound in the form of an oil.

Infrared absorption spectrum (cm⁻¹, neat): 3500, 3400, 1650.

Mass spectrum: 303 (M+).

Elementary analysis values as $C_{20}H_{33}ON$: Calculated: C=79.15%, H=10.96, N=4.62%. Found: C=79.04%, H=11.08%, N=4.70%.

NMR spectrum (δ, CDCl₃): 1.64 (9H, s), 1.72 (3H, s), 1.92 (3H, s), 2.0–2 (12H, m), 5.0–5.2 (3H, m), 5.7 (1H, s), 5.8 (1H, s), 6.3 (1H, s).

EXAMPLE 60

This Example illustrates the synthesis of N,N-dimethyl-3,7,11,15-tetramethyl-2,6,10,14-hexadecatetraenamide (compound K).

To a suspension of 5 g of 55% sodium hydride in anhydrous tetrahydrofuran was added 28.5 g of N,N-dimethyldiethylphosphonoacetamide, and 16.8 g of farnesylacetone was further added and the mixture was stirred at 50° C. for 2 hours. To the liquid reaction mixture was added 100 ml of water, and the mixture was extracted with n-hexane. The extract was washed with water and dried. The solvent was removed by distillation and the residue was purified by column chromatography using silica gel to obtain 16 g of the intended compound in the form of an oil.

Infrared absorption spectrum (cm⁻¹, neat): 1650.

Mass spectrum: 331 (M+).

Elementary analysis values as $C_{22}H_{37}ON$: Calculated: C=79.70%, H=11.25%, N=4.23%. Found: C=79.61%, H=11.31%, N=4.35%.

NMR spectrum (δ, CDCl₃): 1.64 (9H, s), 1.72 (3H, s), 1.92 (3H, s) 2.0–2.2 (12H, m), 2.98 (3H, s), 3.02 (3H, s), 5.0–5.2 (3H, m), 5.8 (1H, s).

EXAMPLE 61

This Example illustrates the synthesis of 4-(3,7,11,15-tetramethyl-2,6,10,14-hexadecatetraenoyl)morpholine (compound M).

To a suspension of 6.5 g of 55% sodium hydride 100 ml of anhydrous tetrahydrofuran was added 22 g of diethylphosphonoacetomorpholide, and 16.8 g of farnesylacetone was further added and the mixture was stirred at 50° C. for 2 hours. To the liquid reaction mixture was added 100 ml of water and the mixture was extracted with n-hexane. The extract was washed with water and dried. The solvent was removed by distillation and the residue was purified by column chromatography using silica gel to obtain 17.5 g of the intended compound in the form of an oil.

Infrared absorption spectrum (cm⁻¹, neat): 1650, 1100.

Mass spectrum: 237 (M+).

Elementary analysis values as $C_{24}H_{39}O_2N$: Calculated: C=77.16%, H=10.52%, N=3.75%. Found: 77.04%, H=10.47%, N=3.91%.

NMR spectrum (δ, CDCl₃): 1.64 (9H, s), 1.72 (3H, s), 1.92 (3H, s), 2.0–2.2 (12H, m), 3.4–3.8 (8H, m), 5.0–5.2 (3H, m), 5.8 (1H, s).

EXAMPLE 62

This Example illustrates the synthesis of 1-(3,7,11,15-tetramethyl-2,6,10,14-hexadecatetraenoyl)-4-formylpiperazine.

In tetrahydrofuran, 44 g of diethylphosphonoacetato-4-formylpiperazide, 6.5 g of 55% sodium hydride and 28.3 g of farnesylacetone were reacted and treated in the same manner as described in Example 59 to obtain 31 g of the intended compound in the form of an oil.

Infrared absorption spectrum (cm⁻¹, neat): 1680, 1640.

Mass spectrum: 400 (M+).

Elementary analysis values as $C_{25}H_{40}O_2N_2$: Calculated: C=74.95%, H=10.07%, N=6.99%. Found: C=74.81%, H=9.93%, N=6.88%.

NMR spectrum ($\delta$, CDCl$_3$): 1.64 (9H, s), 1.72 (3H, s), 1.92 (3H, s) 2.0–2.2 (12H, m), 2.8–2.9 (4H, m), 3.4–3.7 (4H, m), 5.0–5.2 (3H, m), 5.8 (1H, s), 8.1 (1H, s).

EXAMPLE 63

This example illustrates the synthesis of 1-(3,7,11,15-tetramethyl-2,6,10,14-hexadecatetraenoyl)piperazine.

To 150 ml of anhydrous dimethylsulfoxide containing 3.2 g of 55% sodium hydride was added 30 g of the compound obtained in Example 62, and the mixture was stirred at 100° to 120° C. for 1 hour. The liquid reaction mixture was poured into ice water and the mixture was extracted with n-hexane. The extract was washed with water and dried. The solvent was removed by distillation and the residue was purified by column chromatography using silica gel to obtain 6.5 g of the intended compound in the form of an oil.

Infrared absorption spectrum (cm$^{-1}$, neat): 1640.

Mass spectrum: 327 (M+).

Elementary analysis values as $C_{24}H_{40}ON_2$: Calculated: C=77.36%, H=10.82%, N=7.52%. Found: C=77.18%, H=10.91%, N=7.70%.

NMR spectrum ($\delta$, CDCl$_3$): 1.64 (9H, s), 1.72 (3H, s), 1.92 (3H, s), 2.0–2.2 (12H, m), 2.8–2.9 (4H, m), 3.4–3.7 (4H, m), 5.0–5.2 (3H, m), 5.8 (1H, s).

EXAMPLE 64

This Example illustrates the synthesis of 1-(3,7,11,15-tetramethyl-2,6,10,14-hexadecatetraenoyl)-4-(2-hydroxyethyl)piperazine (compound L).

In tetrahydrofuran, 37 g of diethylphosphonoacetato-4-(2-hydroxyethyl)piperazide, 4.2 g of 55% sodium hydride and 21 g of farnesylacetone were reacted and treated in the same manner as described in Example 59 to obtain 12 g of the intended compound in the form of an oil.

Infrared absorption spectrum (cm$^{-1}$, neat): 3400, 1650.

Mass spectrum: 416 (M+).

Elementary analysis values as $C_{26}H_{44}O_2N_2$: Calculated: C=74.95%, H=10.65%, N=6.72%. Found: C=74.77%, H=10.52%, N=6.88%.

NMR spectrum ($\delta$, CDCl$_3$): 1.64 (9H, s), 1.72 (3H, s), 1.92 (3H, s), 2.0–2.2 (12H, m), 2.4–2.6 (6H, m), 3.04 (1H, s), 3.4–3.7 (6H, m), 5.0–5.2 (3H, m), 5.8 (1H, s).

EXAMPLE 65

This Example illustrates the synthesis of N-(2,6-dimethylphenyl)-3,7,11,15-tetramethyl-2,6,10,14-hexadecatetraenamide.

In tetrahydrofuran, 24 g of diethylphosphono-α-(2,6-dimethylphenyl)acetamide, 3.3 g of 55% sodium hydride and 15 g of farnesylacetone were reacted and treated in the same manner as described in Example 59 to obtain 14 g of the intended compound in the form of an oil.

Infrared absorption spectrum (cm$^{-1}$, neat): 3250, 1650.

Mass spectrum: 407 (M+).

Elementary analysis values as $C_{28}H_{41}ON$: Calculated: C=82.50%, H=10.14%, N=3.44%. Found: C=82.72%, H=10.21%, N=3.29%.

NMR spectrum ($\delta$, CDCl$_3$): 1.64 (9H, s), 1.72 (3H, s), 1.92 (3H, s), 2.0–2.2 (12H, m), 2.2 (6H, s), 5.0–5.2 (3H, m), 5.8 (1H, s), 7.02 (3H, s), 7.5 (1H, s).

EXAMPLE 66

This Example illustrates the synthesis of 4-(3,7,11,15-tetramethyl-2-hexadecaenoyl)morpholine (compound I).

In tetrahydrofuran, 22 g of diethylphosphonoacetomorpholide, 5 g of 55% sodium hydride and 17 g of 3,7,10-trimethyldodecanylacetone were reacted and treated in the same manner as in Example 59 to obtain 17 g of the intended compound in the form of an oil.

Infrared absorption spectrum (cm$^{-1}$, neat): 1640, 1100.

Mass spectrum: 379 (M+).

Elementary analysis values as $C_{24}H_{45}O_2N$: Calculated: C=75.93%, H=11.95%, N=3.69%. Found: C=75.99%, H=11.88%, N=3.74%.

NMR spectrum ($\delta$, CDCl$_3$): 0.9–1.0 (12H, m), 1.0–1.8 (21H, m), 1.92 (3H, s), 3.4–3.6 (8H, m), 5.8 (1H, s).

EXAMPLE 67

This Example illustrates the synthesis of 4-(3,7,11-trimethyl-2,6,10-dodecatrienoyl)morpholine.

In tetrahydrofuran, 18 g of diethylphosphonoacetomorpholide, 5.2 g of 55% sodium hydride and 8.8 g of geranylacetone were reacted and treated in the same manner as described in Example 59 to obtain 9.4 g of the intended compound in the form of an oil.

Infrared absorption spectrum (cm$^{-1}$, neat): 1650, 1100.

Mass spectrum: 305 (M+).

Elementary analysis values as $C_{19}H_{31}O_2N$: Calculated: C=74.71%, H=10.23%, N=4.59%. Found: C=74.82%, H=10.11%, N=4.63%.

NMR spectrum ($\delta$, CDCl$_3$): 1.64 (6H, s), 1.72 (3H, s), 1.92 (3H, s), 2.0–2.2 (8H, m), 3.4–3.8 (8H, m), 5.0–5.2 (2H, m), 5.8 (1H, s).

Compounds of Examples 68 to 100 were synthesized in the same manner as described in Examples 59 to 67 according to the process B described hereinafter. These compounds are shown in Table 6. In Table 6, the symbol "————" in column "a, b" indicates that a and b together define a direct valence bond between the carbon atoms to which they are attached.

TABLE 6

$$H{\leftarrow}CH_2-\underset{\underset{a}{|}}{\overset{\overset{CH_3}{|}}{C}}-\underset{\underset{b}{|}}{CH}-CH_2{\rightarrow}_n CH_2-\overset{\overset{CH_3}{|}}{C}=CH-CON\overset{R_1}{\underset{R_2}{\diagdown}}$$ (I-2)

| Example No. | n | a | b | $-N\diagdown^{R_1}_{R_2}$ | Molecular Formula and State | Elementary Analysis Values [calculated (%) / found (%)] C | H | N | Mass Spectrum (M+) | NMR Spectrum (δ, CDCl₃) |
|---|---|---|---|---|---|---|---|---|---|---|
| 68 | 1 | — | — | —NH₂ | C₁₀H₁₇ON, oil | 71.81 / 71.69 | 10.25 / 10.20 | 8.38 / 8.45 | 167 | 1.64(3H,s), 1.72(3H,s), 1.92(3H,s), 2.18–2.24 (4H,m), 5.0–5.2(1H,m), 5.7(1H,s), 5.8(1H,s), 6.3(1H,s) |
| 69 | 1 | — | — | —NHCH₃ | C₁₁H₁₉ON, oil | 72.88 / 72.69 | 10.57 / 10.63 | 7.73 / 7.82 | 181 | 1.64(3H,s), 1.72(3H,s), 1.92(3H,s), 2.18–2.24 (4H,m), 3.0(3H,s), 5.0–5.2(1H,m), 5.5(1H,s), 5.8(1H,s) |
| 70 | 1 | — | — | —N(CH₃)₂ | C₁₂H₂₁ON, oil | 73.79 / 73.90 | 10.84 / 10.79 | 7.17 / 7.20 | 195 | 1.64(3H,s), 1.72(3H,s), 1.92(3H,s), 2.18–2.24 (4H,m), 2.98(3H,s), 3.02(3H,s), 5.0–5.2(1H,m), 5.8(1H,s) |
| 71 | 1 | — | — | —N(piperidinyl) | C₁₄H₂₃ON, oil | 75.97 / 75.88 | 10.47 / 10.52 | 6.33 / 6.27 | 221 | 1.4–2.7(4H,m), 1.64(3H,s), 1.72(3H,s), 1.92(3H,s), 2.18–2.24(4H,m), 3.2–4.7 (4H,m), 5.0–5.2(1H,m), 5.8(1H,s) |
| 72 | 1 | — | — | —N(hexahydroazepinyl) | C₁₅H₂₅ON, oil | 76.54 / 76.66 | 10.71 / 10.61 | 5.95 / 5.99 | 235 | 1.4–2.7(6H,m), 1.64(3H,s), 1.72(3H,s), 1.92(3H,s), 2.18–2.24(4H,m), 3.2–4.7 (4H,m), 5.0–5.2(1H,m), 5.8(1H,s) |
| 73 | 1 | — | — | —N(morpholinyl) | C₁₄H₂₃O₂N, oil | 70.85 / 70.99 | 9.77 / 9.65 | 5.90 / 5.98 | 237 | 1.64(3H,s), 1.72(3H,s), 1.92(3H,s), 2.18–2.24(4H,m), 3.4–3.8(8H,m), 5.0–5.2 (1H,m), 5.8(1H,s) |
| 74 | 1 | — | — | —N(piperazinyl)N—CHO | C₁₅H₂₄O₂N₂, oil | 68.15 / 68.03 | 9.15 / 9.02 | 10.60 / 10.71 | 264 | 1.64(3H,s), 1.72(3H,s), 1.92(3H,s), 2.0–2.2(4H,m), 2.8–2.9(4H,m), 3.4–3.7 (4H,m), 5.0–5.2(1H,m), 5.8 (1H,s), 8.1(1H,s) |
| 75 | 1 | — | — | —N(piperazinyl)NH | C₁₄H₂₄ON₂, oil | 71.14 / 71.00 | 10.24 / 10.18 | 11.85 / 11.94 | 236 | 1.64(3H,s), 1.72(3H,s), 1.92(3H,s), 2.18–2.24(4H,m), 2.8–2.9(4H,m), 3.4–3.7(4H,m), 5.0–5.2(1H,m), 5.8(1H,s) |
| 76 | 1 | — | — | —N(piperazinyl)N—(CH₂)₂OH | C₁₆H₂₈O₂N₂, oil | 68.53 / 68.41 | 10.07 / 10.15 | 9.99 / 10.08 | 280 | 1.64(3H,s), 1.72(3H,s), 1.92(3H,s), 2.18–2.24(4H,m), 2.4–2.6(6H,m), 3.04(1H,s), 3.4–3.7(6H,m), 5.0–5.2 (1H,s), 5.8(1H,s) |
| 77 | 1 | — | — | —NH-(2,6-dimethylphenyl) | C₁₈H₂₅ON, oil | 79.66 / 79.80 | 9.29 / 9.19 | 5.16 / 5.22 | 271 | 1.64(3H,s), 1.72(3H,s), 1.92(3H,s), 2.18–2.24(4H,m), 2.2(6H,s), 5.0–5.2(1H,m), 5.8(1H,s), 7.02(3H,s), 7.5(1H,s) |
| 78 | 2 | — | — | —NH₂ | C₁₅H₂₅ON, oil | 76.54 / 76.42 | 10.71 / 10.64 | 5.95 / 5.99 | 235 | 1.64(6H,s), 1.72(3H,s), 1.92(3H,s), 2.0–2.2(8H,m), 5.0–5.2(2H,m), 5.7(1H,s), 5.8(1H,s), 6.3(1H,s) |

TABLE 6-continued $$H\text{-}(CH_2\text{-}\underset{a}{\underset{|}{C}}(CH_3)\text{-}\underset{b}{\underset{|}{CH}}\text{-}CH_2)_{\overline{n}}CH_2\text{-}C(CH_3)=CH\text{-}CON\underset{R_2}{\overset{R_1}{\diagup}}$$ (I-2)

| Example No. | n | a | b | $-N\overset{R_1}{\underset{R_2}{\diagup}}$ | Molecular Formula and State | Elementary Analysis Values calculated (%) / found (%) | | | Mass Spectrum (M+) | NMR Spectrum (δ, CDCl$_3$) |
|---|---|---|---|---|---|---|---|---|---|---|
| | | | | | | C | H | N | | |
| 79 | 2 | — | — | —NHCH$_3$ | C$_{16}$H$_{27}$ON, oil | 77.06 / 77.15 | 10.91 / 10.80 | 5.62 / 5.73 | 249 | 1.64(6H,s), 1.72(3H,s), 1.92(3H,s), 2.0–2.2(8H,m), 3.0(3H,s), 5.0–5.2(2H,m), 5.5(1H,s), 5.8(1H,s), |
| 80 | 2 | — | — | —N(CH$_3$)$_2$ | C$_{17}$H$_{29}$ON, oil | 77.51 / 77.60 | 11.08 / 11.12 | 5.33 / 5.29 | 263 | 1.64(6H,s), 1.72(3H,s), 1.92(3H,s), 2.0–2.2(8H,m), 2.98(3H,s), 3.02(3H,s), 5.0–5.2(2H,m), 5.8(1H,s) |
| 81 | 2 | — | — | 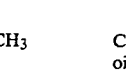 | C$_{19}$H$_{31}$ON, oil | 78.84 / 78.70 | 10.80 / 10.91 | 4.84 / 4.72 | 289 | 1.4–2.7(4H,m), 1.64(6H,s), 1.72(3H,s), 1.92(3H,s), 2.0–2.2(8H,m), 3.2–4.7 (4H,m), 5.0–5.2(2H,m), 5.8(1H,s) |
| 82 | 2 | — | — |  | C$_{20}$H$_{33}$ON, oil | 79.15 / 79.02 | 10.96 / 10.81 | 4.62 / 4.75 | 303 | 1.4–2.7(6H,m), 1.64(6H,s), 1.72(3H,s), 1.92(3H,s), 2.0–2.2 (8H,m), 3.2–4.7(4H,m), 5.0–5.2 (2H,m), 5.8(1H,s) |
| 83 | 2 | — | — | 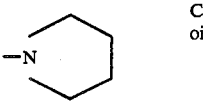 (—N  N—CHO) | C$_{20}$H$_{32}$O$_2$N$_2$, oil | 72.25 / 72.11 | 9.70 / 9.62 | 8.43 / 8.56 | 332 | 1.64(6H,s), 1.72(3H,s), 1.92(3H,s), 2.0–2.2(8H,m), 2.8–2.9(4H,m), 3.4–3.7(4H,m), 5.0–5.2(2H,m), 5.8(1H,s), 8.1(1H,s) |
| 84 | 2 | — | — | 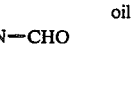 (—N  NH) | C$_{19}$H$_{32}$ON$_2$, oil | 74.95 / 74.78 | 10.59 / 10.48 | 9.20 / 9.33 | 304 | 1.64(6H,s), 1.72(3H,s), 1.92(3H,s), 2.0–2.2(8H,m), 2.8–2.9(4H,m), 3.4–3.7(4H,m), 5.0–5.2(2H,m), 5.8(1H,s) |
| 85 | 2 | — | — | 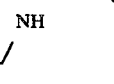 (—N  N—(CH$_2$)$_2$OH) | C$_{21}$H$_{36}$O$_2$N$_2$, oil | 72.37 / 72.52 | 10.41 / 10.35 | 8.04 / 8.11 | 348 | 1.64(6H,s), 1.72(3H,s), 1.92(3H,s), 2.0–2.2(8H,m), 2.4–2.6(6H,m), 3.04(1H,s), 3.4–3.7(6H,m), 5.0–5.2 (2H,m), 5.8(1H,s) |
| 86 | 2 | — | — | 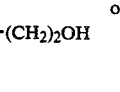 (2,6-dimethylphenyl-NH—) | C$_{23}$H$_{33}$ON, oil | 81.36 / 81.27 | 9.80 / 9.91 | 4.13 / 4.08 | 339 | 1.64(6H,s), 1.72(3H,s), 1.92(3H,s), 2.0–2.2(8H,m), 2.2(6H,s), 5.0–5.2(2H,m), 5.8(1H,s), 7.02(3H,s), 7.5 (1H,s) |
| 87 | 3 | — | — | —NHCH$_3$ | C$_{21}$H$_{35}$ON, oil | 79.44 / 79.52 | 11.11 / 11.15 | 4.41 / 4.30 | 317 | 1.64(9H,s), 1.72(3H,s), 1.92(3H,s), 2.0–2.2(12H,m), 3.0(3H,s), 5.0–5.2(3H,m), 5.5(1H,s), 5.8(1H,s) |
| 88 | 3 | — | — | 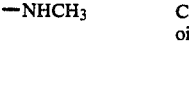 | C$_{24}$H$_{39}$ON, oil | 80.61 / 80.75 | 10.99 / 10.87 | 3.92 / 3.99 | 357 | 1.3–2.7(4H,m), 1.64(9H,s), 1.72(3H,s), 1.92(3H,s), 2.0–2.2 (12H,m), 3.4–4.7(4H,m), 5.0–5.2(3H,m), 5.8(1H,s) |
| 89 | 3 | — | — | 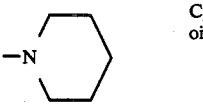 | C$_{25}$H$_{41}$ON, oil | 80.80 / 80.96 | 11.12 / 11.15 | 3.77 / 3.64 | 371 | 1.4–2.7(4H,m), 1.64(9H,s), 1.72(3H,s), 1.92(3H,s), 2.0–2.2 (12H,m), 3.2–4.7(4H,m), 5.0–5.2 (3H,m), 5.8(1H,s), |

TABLE 6-continued $$H{-}CH_2{-}\underset{a}{\overset{CH_3}{C}}{-}\underset{b}{CH}{-}CH_2{\xrightarrow{}_n}CH_2{-}\overset{CH_3}{C}{=}CH{-}CON\overset{R_1}{\underset{R_2}{\diagdown}} \qquad (I\text{-}2)$$

| Example No. | n | a | b | $-N\diagup^{R_1}_{R_2}$ | Molecular Formula and State | Elementary Analysis Values calculated (%) / found (%) C | H | N | Mass Spectrum (M⁺) | NMR Spectrum (δ, CDCl₃) |
|---|---|---|---|---|---|---|---|---|---|---|
| 90 | 4 | — | — | —NH₂ | C₂₅H₄₁ON, oil | 80.80 / 80.64 | 11.12 / 11.22 | 3.77 / 3.89 | 371 | 1.64(12H,s), 1.72(3H,s), 1.92 (3H,s), 2.0–2.2(16H,m), 5.0–5.2 (4H,m), 5.7(1H,s), 5.8(1H,s), 6.3(1H,s) |
| 91 | 4 | — | — | —NHCH₃ | C₂₆H₄₃ON, | 80.98 / 80.72 | 11.24 / 11.21 | 3.63 / 3.75 | 385 | 1.64(12H,s), 1.72(3H,s), 1.92 (3H,s), 2.0–2.2(16H,m), 3.0 (3H,s), 5.0–5.2(4H,m), 5.5 (1H,s), 5.8(1H,s) |
| 92 | 4 | — | — | —N(CH₃)₂ | C₂₇H₄₅ON, oil | 81.14 / 81.31 | 11.35 / 11.30 | 3.51 / 3.42 | 399 | 1.64(12H,s), 1.72(3H,s), 1.92 (3H,s), 2.0–2.2(16H,m), 2.98 (3H,s) 3.02(3H,s), 5.0–5.2 (4H,m), 5.8(1H,s) |
| 93 | 4 | — | — |  | C₂₉H₄₇ON, oil | 81.82 / 81.96 | 11.13 / 11.21 | 3.29 / 3.14 | 425 | 1.47–2.7(4H,m), 1.64(12H,s), 1.72(3H,s), 1.92(3H,s), 2.0–2.2 (16H,MO, 3.2–4.7(4H,m), 5.0–5.2 (4H,m), 5.8(1H,s) |
| 94 | 4 | — | — |  | C₃₀H₄₉ON, | 81.94 / 81.78 | 11.23 / 11.20 | 3.19 / 3.22 | 439 | 1.4–2.7(6H,m), 1.64(12H,s), 1.72(3H,s), 1.92(3H,s), 2.0–2.2 (16H,m), 3.2–4.7(4H,m), 5.0–5.2(4H,m), 5.8(1H,s) |
| 95 | 4 | — | — |  | C₂₉H₄₇O₂N, oil | 78.86 / 78.78 | 10.73 / 10.84 | 3.17 / 3.22 | 441 | 1.64(12H,s), 1.72(3H,s), 1.92 (3H,s), 2.0–2.2(16H,m), 3.4–3.8(8H,m), 5.0–5.2(4H,m), 5.8(1H,s) |
| 96 | 4 | — | — | 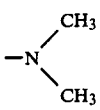 | C₃₀H₄₈O₂N₂, oil | 76.87 / 76.64 | 10.32 / 10.18 | 5.98 / 6.14 | 468 | 1.64(12H,s), 1.72(3H,s), 1.92 (3H,s), 2.0–2.2(16H,m), 2.8–2.9(4H,m), 3.4–3.7(4H,m), 5.0–5.2(4H,m), 5.8(1H,s), 8.1(1H,s) |
| 97 | 4 | — | — |  | C₂₉H₄₈ON₂, oil | 79.03 / 79.14 | 10.93 / 10.80 | 6.36 / 6.46 | 440 | 1.64(12H,s), 1.72(3H,s), 1.92 (3H,s), 2.0–2.2(16H,m), 2.8–2.9(4H,m), 3.4–3.7(4H,m), 5.0–5.2(4H,m), 5.8(1H,s) |
| 98 | 4 | — | — | 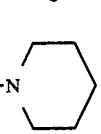 | C₃₁H₅₂O₂N₂, oil | 76.81 / 76.70 | 10.81 / 10.83 | 5.78 / 5.90 | 484 | 1.64(12H,s), 1.72(3H,s), 1.92 (3H,s), 2.0–2.2(16H,m), 2.4–2.6(6H,m), 3.04(1H,s), 3.4–3.7(6H,m), 5.0–5.2 (4H,m), 5.8(1H,s) |
| 99 | 4 | — | — | 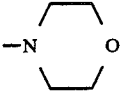 | C₃₃H₄₉ON, oil | 83.31 / 83.12 | 10.38 / 10.29 | 2.94 / 3.11 | 475 | 1.64(12H,s), 1.72(3H,s), 1.92 (3H,s), 2.0–2.2(16H,m), 2.2 (6H,s), 5.0–5.2(4H,m), 5.8 (1H,s), 7.02(3H,s), 7.5(1H,s) |
| 100 | 1 | H | H | —NH₂ | C₁₀H₁₉ON, oil | 70.96 / 70.79 | 11.32 / 11.44 | 8.28 / 8.43 | 169 | 0.9–1.0(6H,m), 1.0–1.8(7H,m), 1.92(3H,s), 5.7(1H,s), 5.8 (1H,s), 6.3(1H,s) |
| 101 | 1 | H | H | 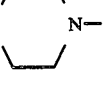 | C₁₄H₂₅O₂N, oil | 70.25 / 70.31 | 10.53 / 10.59 | 5.85 / 5.96 | 239 | 0.9–1.0(6H,m), 1.0–1.8(7H,m), 1.92(3H,s), 3.4–3.6(8H,m), 5.8(1H,s) |

TABLE 6-continued $$H{-}(CH_2{-}\underset{a}{\overset{CH_3}{\underset{|}{C}}}{-}\underset{b}{CH}{-}CH_2)_{\overline{n}}CH_2{-}\overset{CH_3}{\underset{|}{C}}{=}CH{-}CON\overset{R_1}{\underset{R_2}{\diagdown}} \quad (I\text{-}2)$$

| Example No. | n | a | b | $-N\begin{smallmatrix}R_1\\R_2\end{smallmatrix}$ | Molecular Formula and State | Elementary Analysis Values [calculated (%) / found (%)] C | H | N | Mass Spectrum (M+) | NMR Spectrum (δ, CDCl₃) |
|---|---|---|---|---|---|---|---|---|---|---|
| 102 | 1 | H | H | —NH—(2,6-dimethylphenyl) | $C_{18}H_{27}ON$, oil | 79.07 / 79.29 | 9.95 / 9.81 | 5.12 / 5.07 | 273 | 0.9–1.0(6H,m), 1.0–1.8(7H,m), 1.92(3H,s), 2.2(6H,s), 5.8 (1H,s), 7.02(3H,s), 7.5(1H,s) |
| 103 | 2 | H | H | —NH₂ | $C_{15}H_{29}ON$, oil | 75.25 / 75.08 | 12.21 / 12.37 | 5.85 / 5.94 | 239 | 0.9–1.0(9H,m), 1.0–1.8(14H,m), 1.92(3H,s), 5.7(1H,s), 5.8 (1H,s), 6.3(1H,s) |
| 104 | 2 | H | H | —N(morpholino)O | $C_{19}H_{35}O_2N$, oil | 73.73 / 73.62 | 11.40 / 11.32 | 4.53 / 4.70 | 309 | 0.9–1.0(9H,m), 1.0–1.8(14H,m), 1.92(3H,s), 3.4–3.6(8H,m), 5.8(1H,s) |
| 105 | 2 | H | H | —N(2,6-dimethylphenyl) | $C_{23}H_{37}ON$, oil | 80.41 / 80.34 | 10.86 / 10.72 | 4.08 / 4.16 | 343 | 0.9–1.0(9H,m), 1.0–1.8(14H,m), 1.92(3H,s), 2.2(6H,s), 5.8 (1H,s), 7.02(3H,s), 7.5(1H,s) |
| 106 | 3 | H | H | —NH₂ | $C_{20}H_{39}ON$, oil | 77.60 / 77.50 | 12.70 / 12.80 | 4.53 / 4.65 | 309 | 0.9–1.0(12H,m), 1.0–1.8(21H,m), 1.92(3H,s), 5.7(1H,s), 5.8 (1H,s), 6.3(1H,s) |
| 107 | 3 | H | H | —NH—(2,6-dimethylphenyl) | $C_{28}H_{47}ON$, oil | 81.29 / 81.39 | 11.45 / 11.33 | 3.39 / 3.26 | 413 | 0.9–1.0(12H,m), 1.0–1.8(21H,m), 1.92(3H,s), 2.2(6H,s), 5.8 (1H,s), 7.02(3H,s), 7.5(1H,s) |
| 108 | 4 | H | H | —NH₂ | $C_{25}H_{49}ON$, oil | 79.09 / 79.02 | 13.01 / 13.14 | 3.69 / 3.77 | 379 | 0.9–1.0(15H,m), 1.0–1.8(28H,m), 1.92(3H,s), 5.7(1H,s), 5.8 (1H,s), 6.3(1H,s) |
| 109 | 4 | H | H | —N(morpholino)O | $C_{29}H_{55}O_2N$, oil | 77.44 / 77.56 | 12.33 / 12.14 | 3.11 / 3.19 | 449 | 0.9–1.0(15H,m), 1.0–1.8(28H,m), 1.92(3H,s), 3.4–3.6(8H,m), 5.8(1H,s) |
| 110 | 4 | H | H | —NH—(2,6-dimethylphenyl) | $C_{33}H_{57}ON$, oil | 81.92 / 81.77 | 11.88 / 11.74 | 2.90 / 3.08 | 483 | 0.9–1.0(15H,m), 1.0–1.8(28H,m), 1.92(3H,s), 2.2(6H,s), 5.8 (1H,s), 7.02(3H,s), 7.5 (1H,s) |

EXAMPLE 111

(Tablets)

| | |
|---|---|
| Compound of Example 3 | 50 g |
| Silicic anhydride | 30 g |
| Crystalline cellulose | 50 g |
| Corn starch | 36 g |
| Hydroxypropyl cellulose | 10 g |
| Calcium stearate | 4 g |

Tablets were prepared from the above composition according to a conventional procedure so that each tablet contained 180 mg of the composition.

EXAMPLE 112

(Capsules)

| Compound of Example 8 | 50 g |
|---|---|
| Silicic anhydride | 35 g |
| Silicic anhydride hydrate | 5 g |
| Crystalline cellulose | 50 g |
| Hydroxypropyl cellulose | 6 g |
| Corn starch | 49 g |
| Talc | 5 g |

The above composition was granulated and packed in gelatin hard capsules (No. 3) according to a conventional procedure so that each capsule contained 200 mg of the composition.

EXAMPLE 113

(Tablets)

| Compound of Example 61 | 50 g |
|---|---|
| Silicic anhydride | 30 g |
| Crystalline cellulose | 50 g |
| Corn starch | 36 g |
| Hydroxypropyl cellulose | 10 g |
| Calcium stearate | 4 g |

Tablets were prepared from the above composition according to a conventional procedure so that each tablet contained 180 mg of the composition.

EXAMPLE 114

| Compound of Example 66 | 50 g |
|---|---|
| Silicic anhydride | 35 g |
| Silicic anhydride hydrate | 5 g |
| Crystalline cellulose | 50 g |
| Hydroxypropyl cellulose | 6 g |
| Corn starch | 49 g |
| Talc | 5 g |

The above composition was granulated and packed in gelatin hard capsules (No. 3) according to a conventional procedure so that each capsule contained 200 mg of the composition.

The embodiments of the invention in which an exclusive property or privilege is claimed are defined as follows:

1. A compound having the formula:

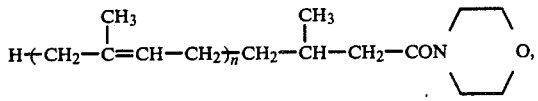

wherein n is an integer of 1 to 4.

2. A compound as set forth in claim 1 which is 4-[(E,E)-3,7,11,15-tetramethyl-6,10,14-hexadecatrienoyl]-morpholine.

3. A compound as set forth in claim 1 which is 4-[(E)-3,7,11-trimethyl-6,10-dodecadienoyl]morpholine.

4. A pharmaceutical composition for treating liver dysfunction which comprises an effective amount of a compound as claimed in claim 1 as an active ingredient, and at least one pharmaceutically acceptable inert carrier or diluent.

* * * * *